US012144687B2

(12) United States Patent
Yoo

(10) Patent No.: US 12,144,687 B2
(45) Date of Patent: Nov. 19, 2024

(54) APPARATUS FOR CORRECTING POSTURE OF ULTRASOUND SCANNER FOR ARTIFICIAL INTELLIGENCE-TYPE ULTRASOUND SELF-DIAGNOSIS USING AUGMENTED REALITY GLASSES, AND REMOTE MEDICAL DIAGNOSIS METHOD USING SAME

(71) Applicant: OMNI C&S Inc, Seoul (KR)

(72) Inventor: Jae-Chern Yoo, Suwon-si (KR)

(73) Assignee: OMNI C&S Inc, Seoul (KR)

( * ) Notice: Subject to any disclaimer, the term of this patent is extended or adjusted under 35 U.S.C. 154(b) by 47 days.

(21) Appl. No.: 17/866,975

(22) Filed: Jul. 18, 2022

(65) Prior Publication Data
US 2022/0387000 A1 Dec. 8, 2022

Related U.S. Application Data

(63) Continuation of application No. PCT/KR2020/019112, filed on Dec. 24, 2020.

(30) Foreign Application Priority Data

Jan. 16, 2020 (KR) .......................... 10-2020-0005799

(51) Int. Cl.
  *A61B 8/00* (2006.01)
  *A61B 90/00* (2016.01)
  *G06T 7/194* (2017.01)

(52) U.S. Cl.
  CPC .............. *A61B 8/54* (2013.01); *A61B 8/4254* (2013.01); *A61B 8/4263* (2013.01);
  (Continued)

(58) Field of Classification Search
  CPC ....... A61B 8/54; A61B 8/4254; A61B 8/4263; A61B 8/4472; A61B 8/462; A61B 8/469;
  (Continued)

(56) References Cited

U.S. PATENT DOCUMENTS 4,127,842 A * 11/1978 Hassler .................. G01P 5/241
                                                      367/90
5,899,861 A *  5/1999 Friemel ............... G01S 7/52074
                                                      600/443
(Continued)

FOREIGN PATENT DOCUMENTS

JP    2012-135679 A    7/2012
JP    2019-514476 A    6/2019
(Continued)

OTHER PUBLICATIONS

Mahmood et al., "Augmented Reality and Ultrasound Education: Initial Experience", 2018 (Year: 2018).*

(Continued)

*Primary Examiner* — Adil Partap S Virk
(74) *Attorney, Agent, or Firm* — NSIP Law

(57) ABSTRACT

An apparatus for correcting a posture of an ultrasound scanner for artificial intelligence-type ultrasound self-diagnosis, includes an ultrasound scanner including an ultrasound probe configured to acquire and transmit an ultrasound image of a patient; a mapper configured to acquire a body map of the patient in which a plurality of virtual interested organs is arranged on a body image; a scanner navigator configured to calculate current position coordinates of the ultrasound scanner on the body map and the ultrasound image; augmented reality glasses configured to display the ultrasound image and a virtual object image; and a processor configured to determine whether the patient has a disease and a risk degree of the disease based on an artificial neural network result of an implemented deep learning neural network trained on ultrasound training images provided with the ultrasound image.

5 Claims, 22 Drawing Sheets

(52) U.S. Cl.
CPC ............ *A61B 8/4472* (2013.01); *A61B 8/462* (2013.01); *A61B 8/469* (2013.01); *A61B 8/56* (2013.01); *G06T 7/194* (2017.01); *A61B 2090/365* (2016.02); *G06T 2207/10132* (2013.01); *G06T 2207/20081* (2013.01); *G06T 2207/20084* (2013.01); *G06T 2207/30004* (2013.01)

(58) Field of Classification Search
CPC ..... A61B 8/56; A61B 2090/365; A61B 8/429; A61B 8/461; A61B 8/5223; A61B 8/565; A61B 8/4245; A61B 8/582; G06T 7/194; G06T 2207/10132; G06T 2207/20081; G06T 2207/20084; G06T 2207/30004; G16H 40/67; G16H 50/50
See application file for complete search history.

(56) References Cited

U.S. PATENT DOCUMENTS

| | | | | |
|---|---|---|---|---|
| 10,702,242 | B2* | 7/2020 | de Jonge | A61B 8/065 |
| 11,861,838 | B1* | 1/2024 | Gardella | G06T 7/0014 |
| 2006/0016006 | A1* | 1/2006 | Whitmore, III | A61B 90/50 |
| | | | | 5/601 |
| 2007/0238981 | A1* | 10/2007 | Zhu | A61B 34/20 |
| | | | | 600/424 |
| 2007/0299342 | A1* | 12/2007 | Hayasaka | A61B 8/00 |
| | | | | 600/443 |
| 2009/0010507 | A1* | 1/2009 | Geng | G06T 7/593 |
| | | | | 382/128 |
| 2009/0036902 | A1* | 2/2009 | DiMaio | A61B 8/12 |
| | | | | 606/130 |
| 2010/0016724 | A1* | 1/2010 | Arai | A61B 8/485 |
| | | | | 600/443 |
| 2010/0179428 | A1* | 7/2010 | Pedersen | G09B 23/286 |
| | | | | 600/443 |
| 2010/0234734 | A1* | 9/2010 | Cho | A61B 8/4461 |
| | | | | 600/459 |
| 2011/0144500 | A1* | 6/2011 | Nihei | A61B 8/4254 |
| | | | | 600/443 |
| 2013/0245428 | A1* | 9/2013 | Banjanin | A61B 8/4263 |
| | | | | 600/424 |
| 2014/0078517 | A1* | 3/2014 | Ben-Yishai | G01B 11/002 |
| | | | | 356/614 |
| 2015/0095069 | A1* | 4/2015 | Waljee | G16H 50/30 |
| | | | | 705/3 |
| 2019/0105016 | A1* | 4/2019 | Jenaro | A61B 8/469 |
| 2019/0231317 | A1* | 8/2019 | Anthony | A61B 8/429 |
| 2020/0161005 | A1* | 5/2020 | Lyman | G16H 50/50 |
| 2020/0265745 | A1* | 8/2020 | Buras | A61B 8/461 |
| 2020/0402236 | A1* | 12/2020 | Courot | G16H 15/00 |
| 2021/0202069 | A1* | 7/2021 | van der Veen | G16H 50/20 |
| 2021/0259765 | A1* | 8/2021 | Narayan | G06N 20/00 |
| 2021/0287804 | A1* | 9/2021 | Barnes | G16H 30/40 |
| 2021/0361261 | A1* | 11/2021 | Noguchi | A61B 8/488 |
| 2022/0387000 | A1* | 12/2022 | Yoo | A61B 8/462 |

FOREIGN PATENT DOCUMENTS

| | | |
|---|---|---|
| KR | 10-2017-0047873 A | 5/2017 |
| KR | 10-2019-0021344 A | 3/2019 |
| WO | WO 2018/180386 A1 | 10/2018 |

OTHER PUBLICATIONS

International Search Report issued on Apr. 7, 2022, in counterpart KR/2020/019112 (4 pages in Korean).

* cited by examiner

FIG. 1C
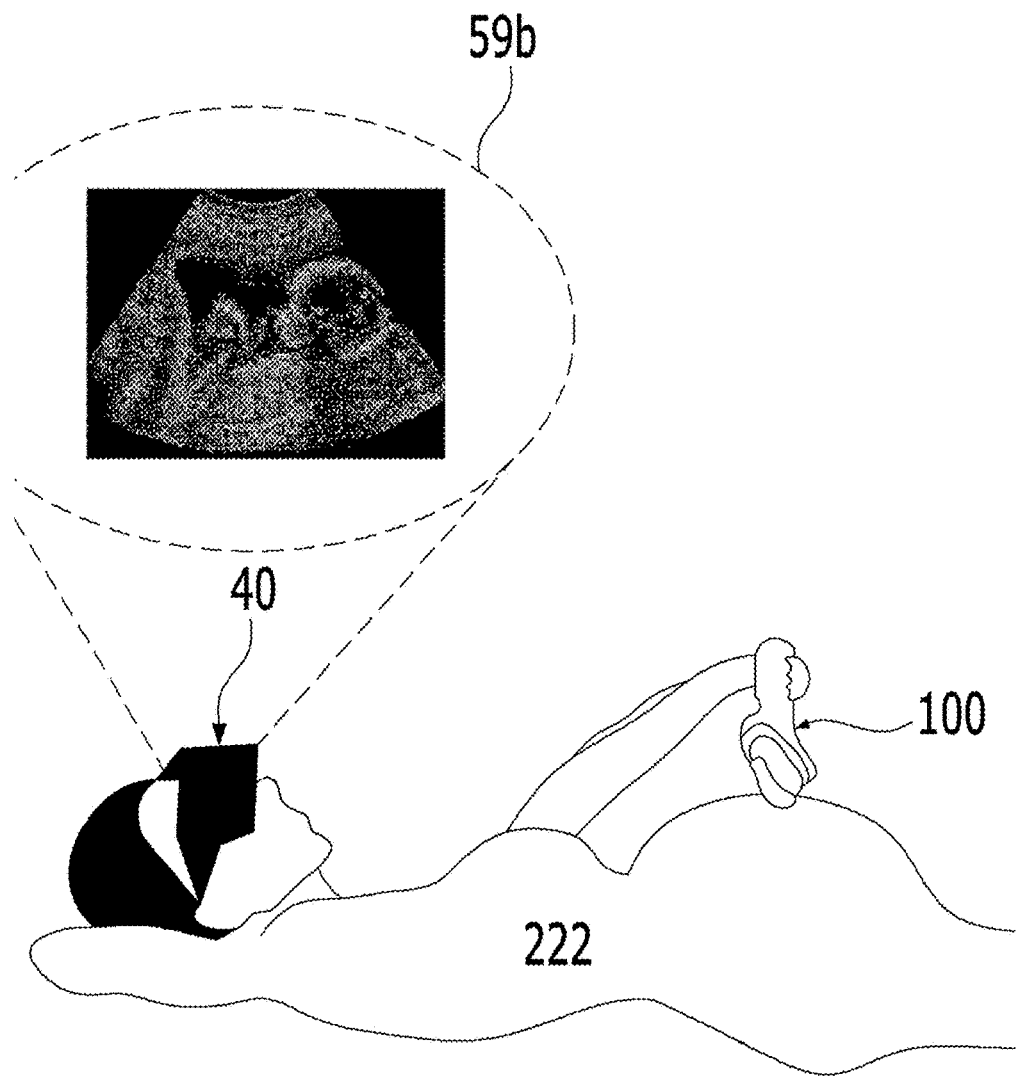
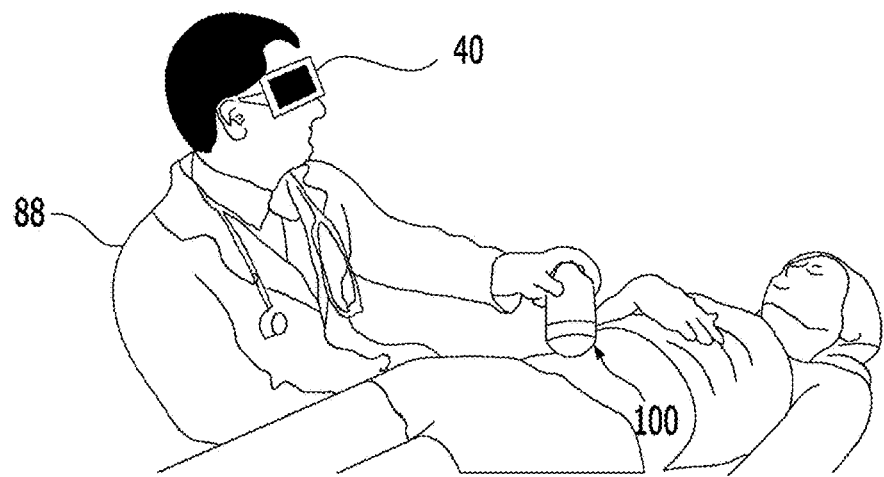

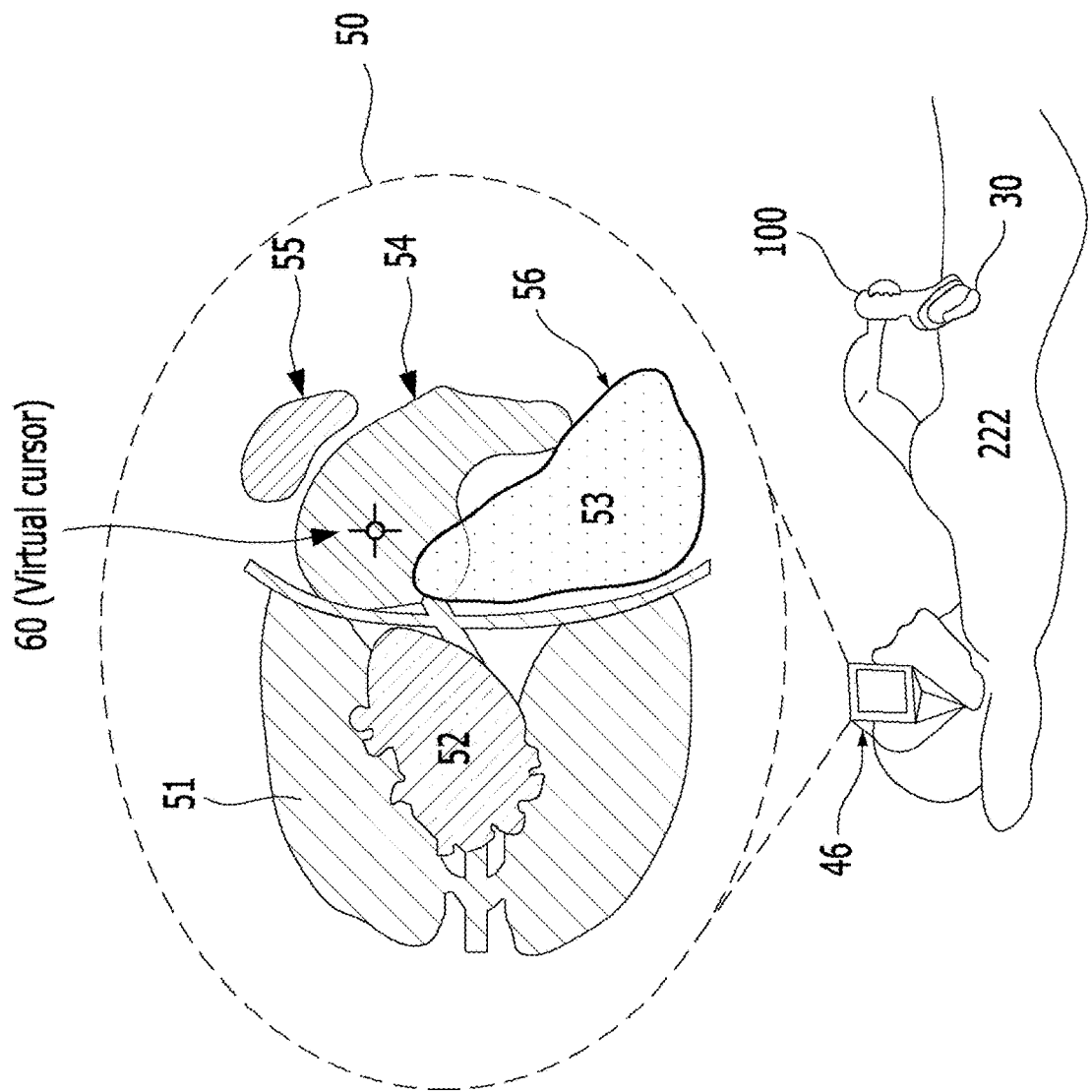

FIG. 3
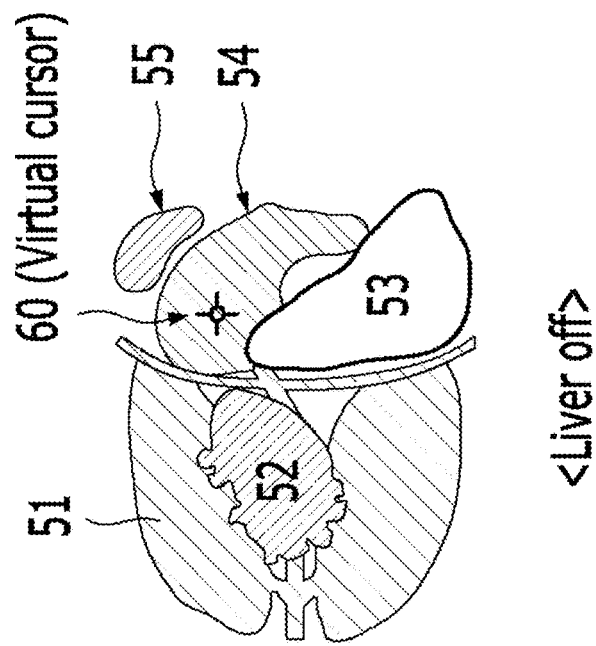
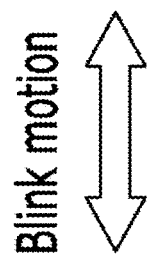
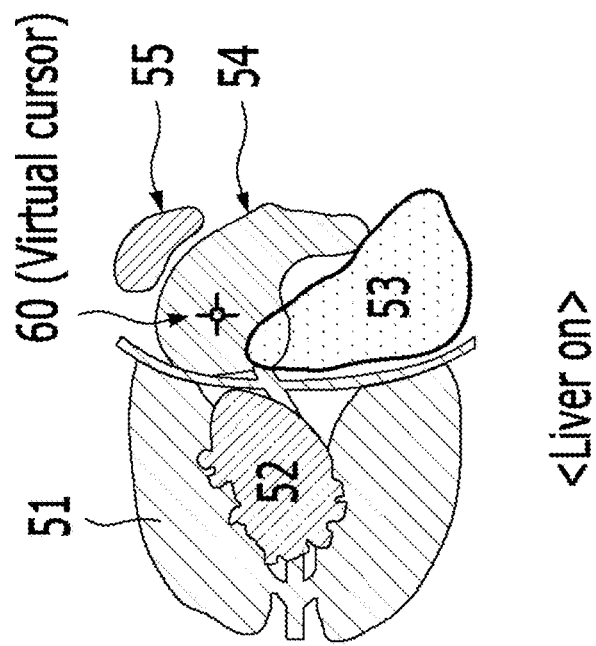

FIG. 11
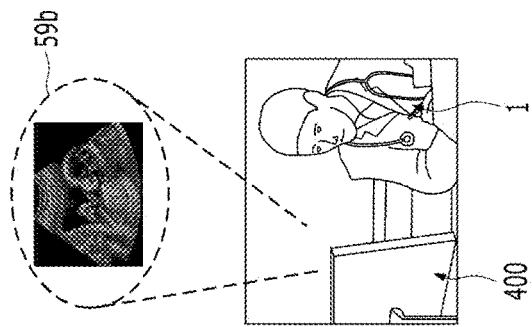
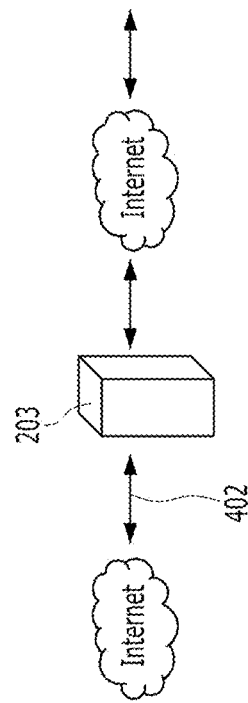
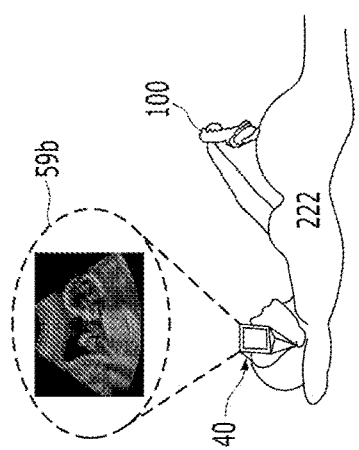

APPARATUS FOR CORRECTING POSTURE OF ULTRASOUND SCANNER FOR ARTIFICIAL INTELLIGENCE-TYPE ULTRASOUND SELF-DIAGNOSIS USING AUGMENTED REALITY GLASSES, AND REMOTE MEDICAL DIAGNOSIS METHOD USING SAME

CROSS-REFERENCE TO RELATED APPLICATIONS

Pursuant to 35 USC 120 and 365(c), this application is a continuation of International Application No. PCT/KR2020/019112 filed on Dec. 24, 2020, which claims the benefit of Korean Patent Application No 10-2020-0005799 filed on Jan. 16, 2020, in the Korean Intellectual Property Office, the entire disclosures of which are incorporated herein by reference for all purposes.

BACKGROUND

1. Field

The following description relates to an apparatus for correcting the posture of an ultrasound scanner for artificial intelligence-type ultrasound self-diagnosis using augmented reality glasses, and remote medical diagnosis method using same.

2. Description of the Related Art

Recently, as digital image processing technology has been applied to the field of clinical diagnosis jointly with medical equipment manufacturing technology, many image medicine advances have been made.

Ultrasound diagnosis is not harmful to the human body because the ultrasound diagnosis can avoid exposure to harmful radiation compared to CT or X-ray medical equipment and can acquire a cross-section photographing image by the human body by a non-invasive method, and is convenient to carry and is low in cost. There is an advantage in that the image can be acquired in real-time, and as a result, a movement state of an organ can be observed in real-time.

Such ultrasound diagnosis technology is widely used in maternal and fetal health diagnosis, fatty liver examination, breast cancer examination, thyroid ultrasound examination, bone density examination, osteoporosis examination, carotid artery ultrasound examination, and the like.

However, if the ultrasound scanner's posture (inclination (incident angle), contact pressure, and location) is not correct during ultrasound diagnosis, it is impossible to obtain a high-quality ultrasound image due to the low resolution of the ultrasound image and the generation of severe noise. Furthermore, since the ultrasound scanner needs to have different contact pressure and incident angle for each affected part, it is virtually difficult to control the posture of such an ultrasound scanner unless it is an experienced expert.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for correcting a posture of an ultrasound scanner for artificial intelligence-type ultrasound self-diagnosis, includes an ultrasound scanner including an ultrasound probe configured to acquire and transmit an ultrasound image of a patient; a mapper configured to acquire a body map of the patient in which a plurality of virtual interested organs is arranged on a body image; a scanner navigator configured to calculate current position coordinates of the ultrasound scanner on the body map and the ultrasound image; augmented reality glasses configured to display the ultrasound image and a virtual object image; and a processor configured to determine whether the patient has a disease and a risk degree of the disease based on an artificial neural network result of an implemented deep learning neural network trained on ultrasound training images provided with the ultrasound image.

The ultrasound scanner may further include a pressure sensor, disposed inside the ultrasound scanner, configured to measure contact pressure between the ultrasound probe and the patient's skin surface, and an inclination sensor configured to recognize an inclination angle of the ultrasound scanner.

The inclination sensor may include liquid channels configured to provide movement paths for an air layer and a liquid layer based on an inclined degree of the ultrasound scanner, vision sensors configured to determine a boundary position between the air layer and the liquid layer, and an angle calculator configured to calculate an inclination of the ultrasound scanner from the boundary position.

The scanner navigator may be configured to observe and determine coordinates of a laser beam, emitted from a laser beam generator of the ultrasound scanner, with a laser angle measuring camera, an infrared camera, or image sensor to obtain the current position coordinates of the ultrasound scanner and display the current position coordinates in the augmented reality glasses using a virtual cursor.

The virtual object image may be any one or any combination of any two or more object images selected from a virtual cursor, pressure correction information, incident angle correction information, a virtual interested organ, and an organ to be examined.

The ultrasound scanner may further include an organ selection click button disposed in the ultrasound scanner. When a user presses the organ selection click button, an examination item may automatically selected by an organ on the body map at a place adjacent to the current coordinates of the ultrasound scanner.

The apparatus may further include a 3D camera, disposed at a position opposite to the patient's bed, configured to perform ultrasound self-diagnosis and acquire the body image.

The mapper may be further configured to use the artificial neural network result to acquire semantic-segmented ultrasound images labeled with different colors for each pixel with respect to the plurality of interested organs, respectively, by performing the semantic segmentation based on the ultrasound image of the patient.

The mapper may be implemented by a body map in which the virtual interested organs are mapped onto the body image acquired from a 3D camera based on a medical arrangement correlation of internal organs of the body.

In another general aspect, a method for correcting a posture of an ultrasound scanner for artificial intelligence-type ultrasound self-diagnosis, including displaying an acquired ultrasound image and a virtual object image using augmented reality glasses; determining whether a patient has a disease and a risk degree information of the disease based on an artificial neural network result of an implemented deep learning neural network trained on ultrasound training images provided with the acquired ultrasound image; receiving a remote medical diagnosis result for the patient generated based on a result of the determination whether the patient has the disease and the risk degree information; and outputting the remote medical diagnosis result through the augmented reality glasses.

Other features and aspects will be apparent from the following detailed description, the drawings, and the claims.

BRIEF DESCRIPTION OF THE DRAWINGS

FIG. 1C illustrates an example of self-diagnosis by using an ultrasound scanner by directly wearing augmented reality glasses according to one or more embodiments.

FIGS. 2A to 2C are examples illustrating an image displayed on a display panel of augmented reality glasses. FIG. 2A illustrates an example of virtual object images labeled with different colors for each organ as virtual interested organs displayed on the display panel of the augmented reality glasses, FIG. 2B illustrates an example expressed by a border line 56 of a liver which is an organ to be examined, and FIG. 2C illustrates an example of overlapping and displaying the border line of an organ to be examined on an ultrasound image when the organ to be examined is the liver 53.

FIG. 3 illustrates an example in which a liver area which is the organ to be examined blinks on/off according to one or more embodiments.

FIG. 11 is an example illustrating a remote medical diagnosis method using an apparatus for correcting a posture of an ultrasound scanner for artificial intelligence-type ultrasound self-diagnosis using augmented reality glasses according to the present disclosure.

Throughout the drawings and the detailed description, the same reference numerals refer to the same or like elements. The drawings may not be to scale, and the relative size, proportions, and depiction of elements in the drawings may be exaggerated for clarity, illustration, and convenience.

DETAILED DESCRIPTION

Figure 1A:
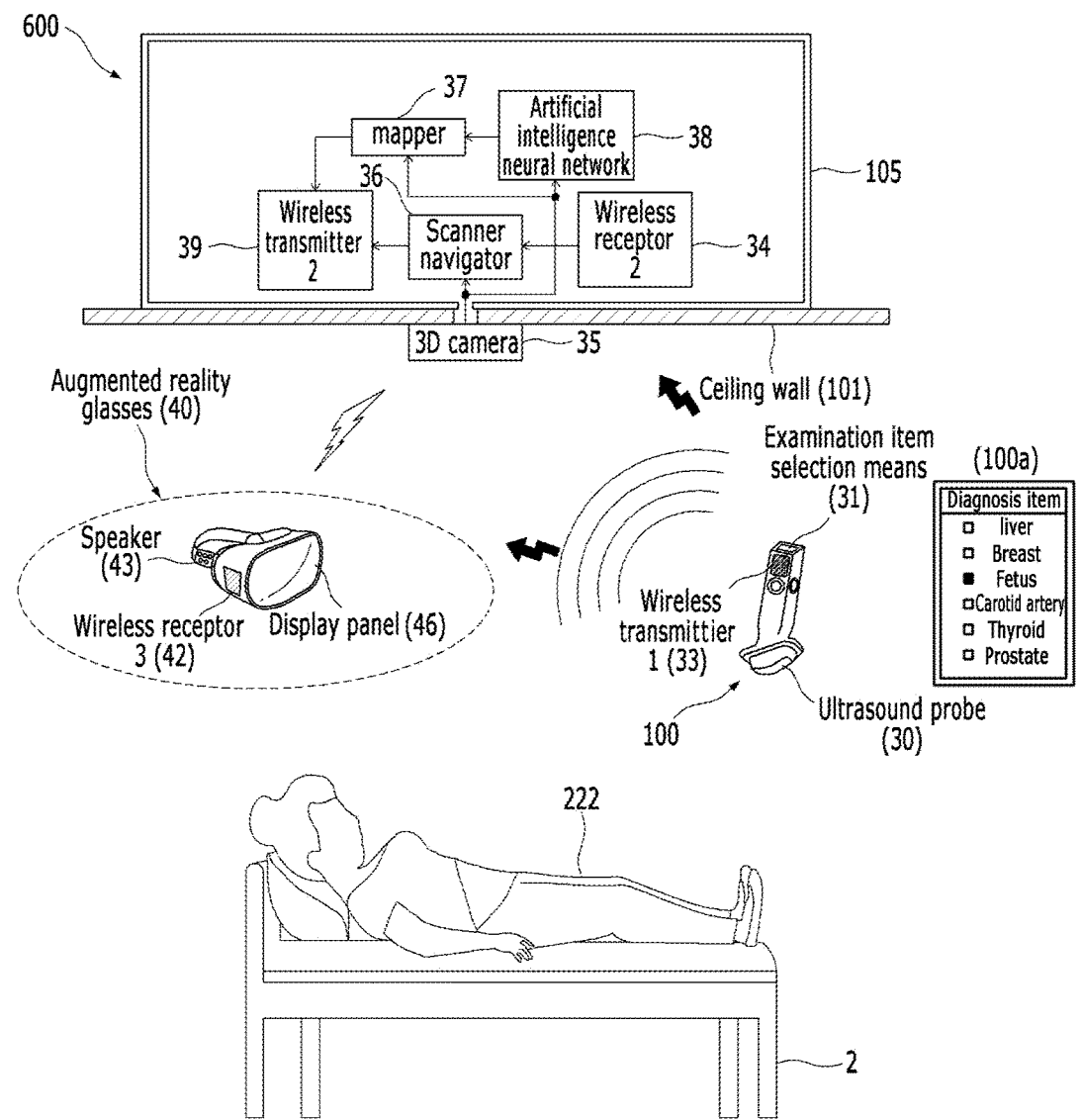
FIGS. 1A and 1B illustrate examples of an apparatus for correcting a posture of an ultrasound scanner according to one or more embodiments.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

FIG. 1A is an example of an ultrasound scanner posture correcting apparatus 600 according to the present disclosure.

Referring to FIG. 1A, the ultrasound scanner posture correcting apparatus 600 may include an examination item selector 31, an ultrasound probe 30, wireless transmitter 1 33, wireless receptor 2 34, a 3D camera 35, a scanner navigator 36, a mapper 37, an artificial neural network 38, wireless transmitter 2 39, an ultrasound scanner 100, augmented reality glasses 40, wireless receptor 3 42, a speaker 43, and a display panel 46.

According to one or more embodiments, the examination item selector 31 may be provided in the ultrasound scanner 100, and may designate an ultrasound examination item.

Further, the ultrasound scanner 100 may include the ultrasound probe 30 for obtaining an ultrasound image from the affected part through contact with the affected part of an examination item patient and the wireless transmitter 1 33 for transmitting ultrasound image information obtained by the ultrasound probe 30 and posture information of the ultrasound probe 30 to the outside.

Further, the wireless receptor 2 34 may receive the ultrasound image information and the posture information of the ultrasound probe 30 from the wireless transmitter 1 33.

Further, the 3D camera 35 may observe the posture and the position of the body of the patient in three dimensions, and reproduce and configure the resulting body image of the patient in real-time.

Further, the mapper 37 may acquire a body map in which virtual interested organs are arranged on the body image.

In addition, the scanner navigator 36 may calculate the coordinates of the current position of the ultrasound scanner on the body image or the ultrasound image.

In addition, a pressure sensor (not illustrated) is mechanically connected and disposed within the ultrasound scanner 100 to measure contact pressure indicating how strong the ultrasound probe 30 presses and scans the affected part of the patient under pressure.

Further, an inclination sensor (not illustrated) may be used to measure an incident angle of the ultrasound scanner 100.

In addition, the wireless transmitter 2 39 may be used for transmitting posture information of the ultrasound scanner, which includes the current position coordinates of the ultrasound scanner measured by the scanner navigator 36, contact pressure information measured by the pressure sensor, and incident angle information measured by the inclination sensor.

Further, the speaker 43 may transfer a feedback control command to a patient 222 or inform the patient 222 of guidance and instructions for ultrasound diagnosis by voice in order to derive the posture of the ultrasound scanner 100 optimized (customized) for each examination item or each examination site by checking the posture information (the current position, the contact pressure, and the incident angle) of the ultrasound scanner 100.

Further, the augmented reality glasses 40 may include the wireless receptor 3 42 for receiving the ultrasound image information transmitted by the wireless transmitter 1 33 and the wireless transmitter 2 39, and the posture information of the ultrasound probe 30, and the display panel 46 displaying the ultrasound images received by the wireless receptor 3 42 and the posture information of the ultrasound scanner 100.

Further, the artificial neural network 38 may perform deep-learning training by inputting ultrasound pictures for training.

The ultrasound scanner posture correcting apparatus 600 uses the artificial neural network 38 subjected to the deep learning training with the ultrasound image of the patient 222 input from the ultrasound probe 30 to automatically discriminate whether the patient 222 has a disease and a disease degree of the patient 222.

The 3D camera 35 may desirably be attached to a ceiling wall 101 above a bed 2 on which the patient 222 lies and self-diagnoses to observe that the patient 222.

The scanner navigator 36, the mapper 37, the artificial neural network 38, the wireless receptor 2 34 and the wireless transmitter 2 39 are hidden inside the ceiling wall 101 and assembled in a plastic case 105, and installed and fixed.

Figure 1B:
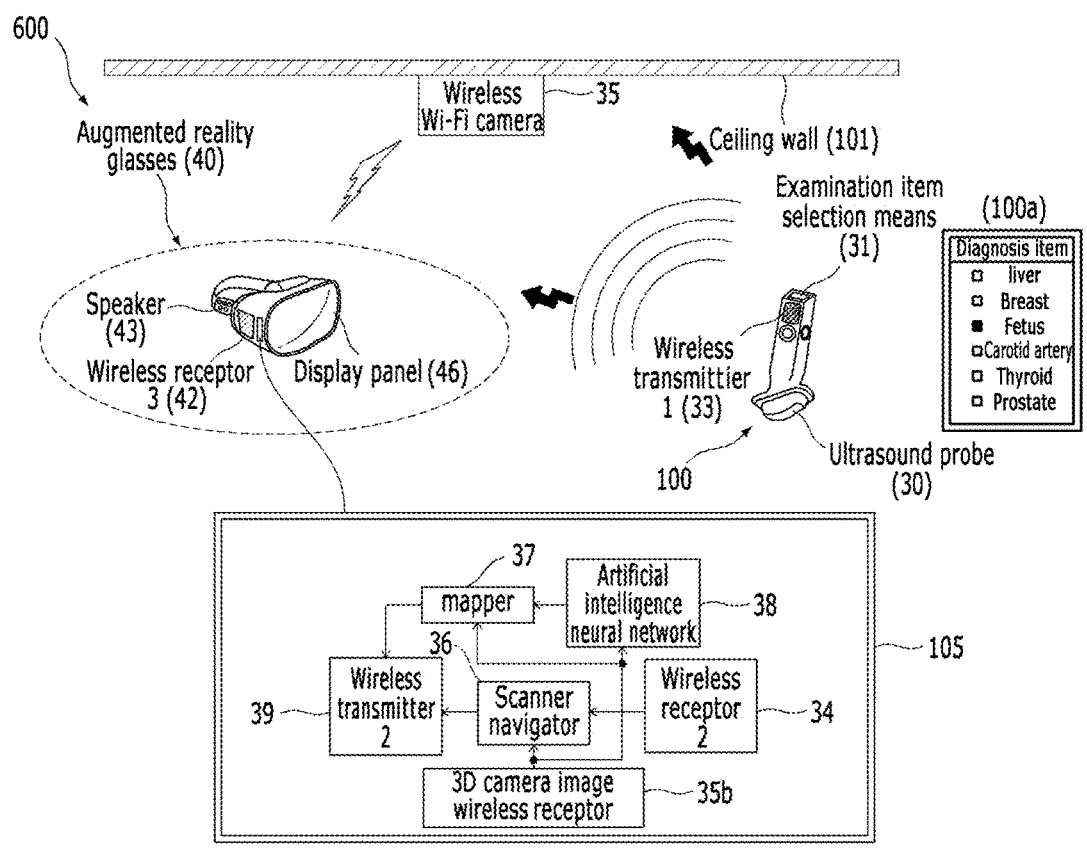

FIG. 1B is an example for describing another aspect of the plastic case 105 and the 3D camera 35, and is characterized in that a wireless Wi-Fi camera is used for the 3D camera 35, and a 3D camera image wireless receptor 35b for receiving image information transmitted from the wireless Wi-Fi camera is further provided in the plastic case 105, and integrated and installed in the augmented reality glasses 40 instead of being concealed inside the ceiling wall 101. In this case, the wireless transmitter 2 39 may not be desired.

Another aspect of the plastic case 105 and the 3D camera 35 is characterized in that the wireless Wi-Fi camera capable of wireless transmission is used as the 3D camera 35, and the 3D camera image wireless receptor 35b for receiving image information transmitted from the wireless Wi-Fi camera is further provided in the plastic case 105, and installed in the form of a separate set-top box instead of being concealed inside the ceiling wall 101.

Reference numeral 100a of FIG. 1A shows an example in which self-diagnosis items are listed and displayed on a touch screen when the touch screen is used as the examination item selector 31.

In the embodiment, the display panel 46 of the augmented reality glasses overlaps a 3D virtual object image on the ultrasound image and shows the relevant image to a person who conducts self-diagnosis, and the virtual object image may desirably be any one or more virtual object images selected from a virtual cursor, pressure correction information, incident angle correction information, and a virtual interested organ.

The wireless transmitter 2 39 transmits the body map acquired by the mapper 37 to the wireless receptor 3 42 to be displayed on the display panel 46 of the augmented reality glasses 40.

The augmented reality glasses 40 of the present disclosure may be replaced by virtual reality glasses.

An upper diagram of FIG. 10 shows an example in which the patient 222 directly wears the augmented reality glasses 40 and performs the self-diagnosis using the ultrasound scanner 100, while a lower diagram of FIG. 10 shows an example in which a person 88 who assists the diagnosis assists the diagnosis by wearing the augmented reality glasses 40 instead. Reference numeral 59b represents an example in which the ultrasound image acquired by the ultrasound scanner 100 is displayed on the display panel of the augmented reality glasses 40.

Figure 1D:
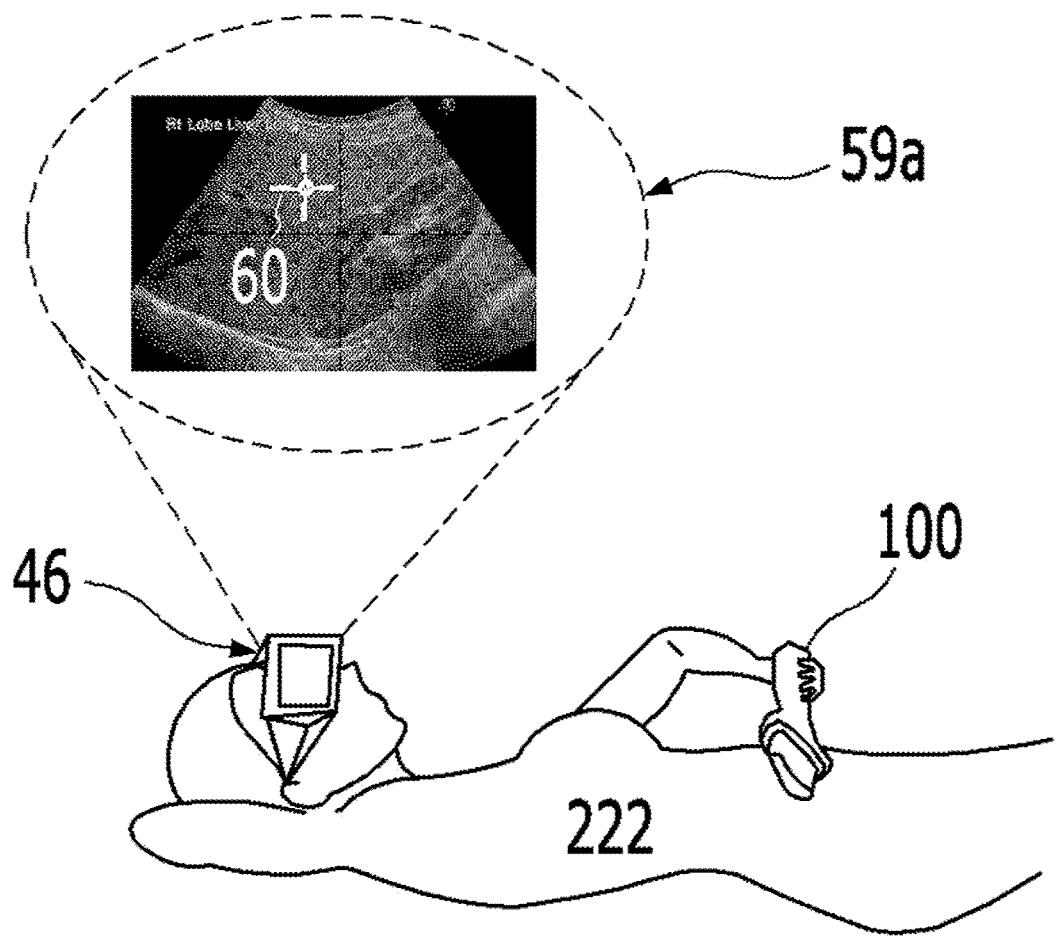
FIG. 1D to FIG. 1G illustrate various examples of self-diagnosis using an ultrasound scanner by the patient wearing augmented reality glasses, according to one or more embodiments.
Figure 1E:
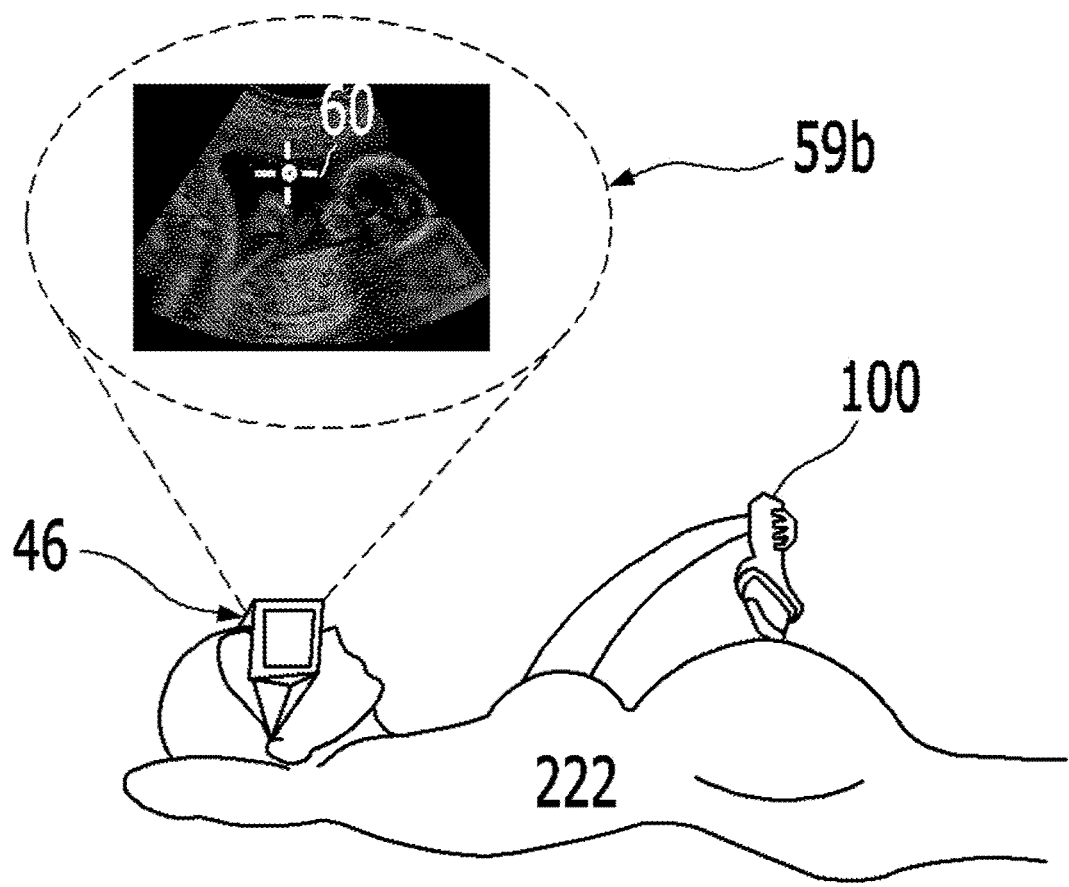
Figure 1F:
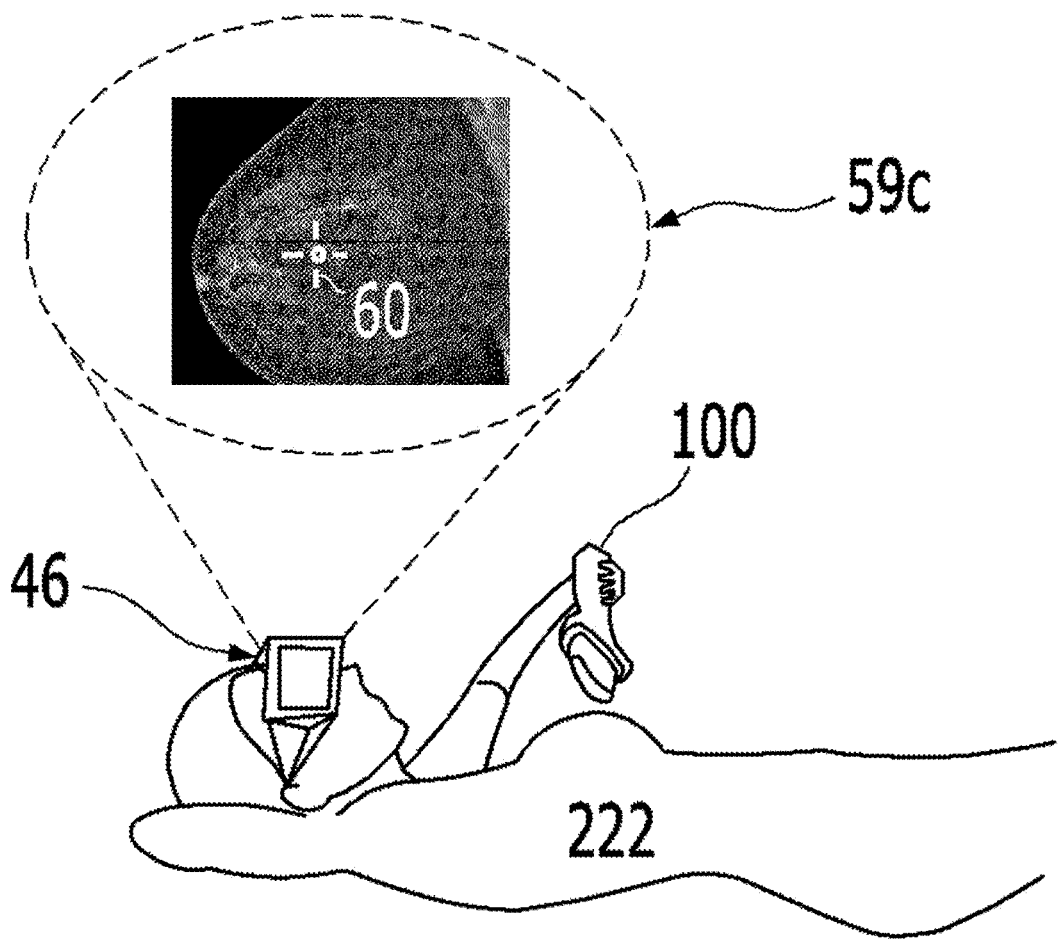
Figure 1G:
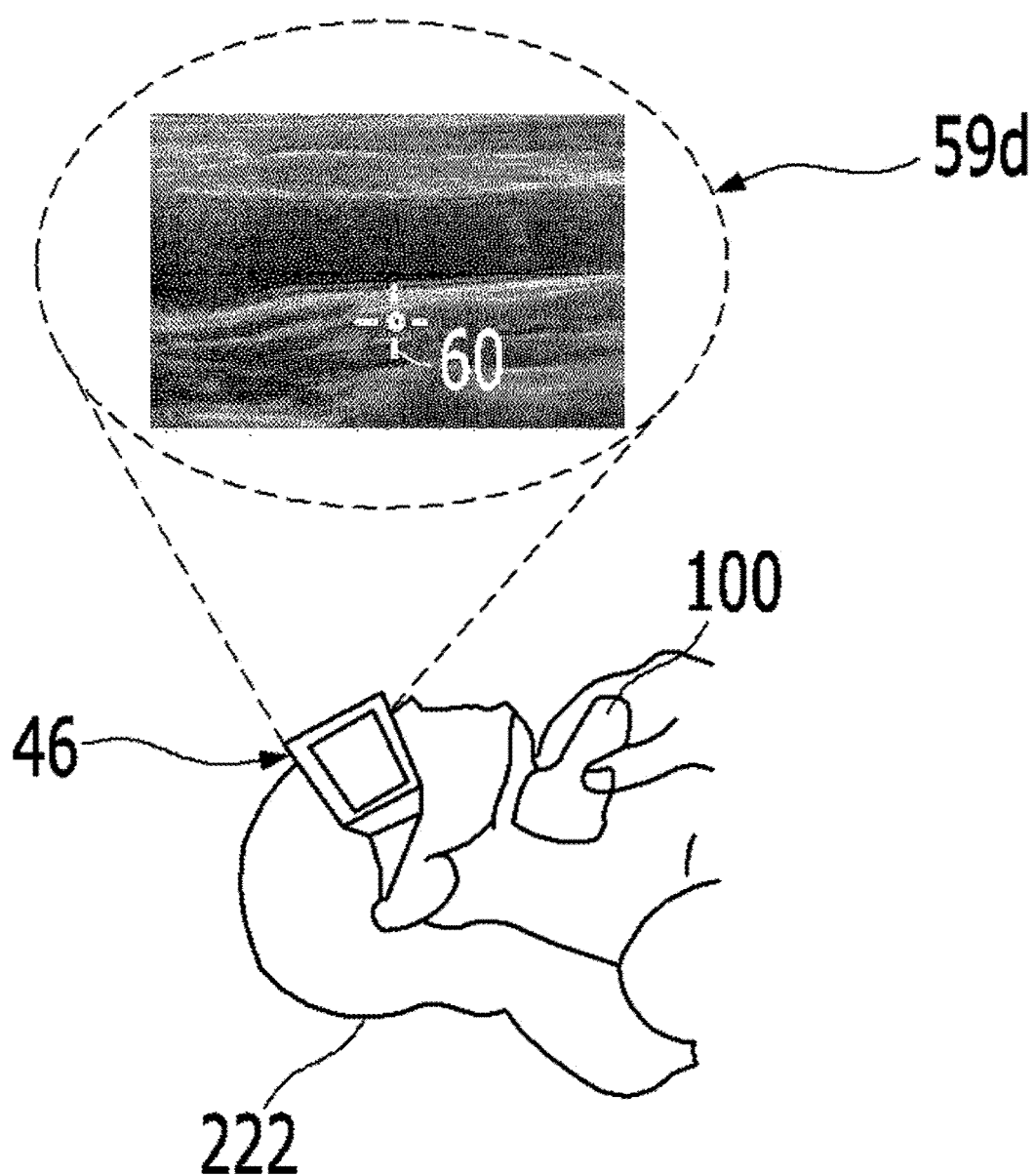

FIG. 1D to FIG. 1G illustrates various examples in which the patient 222 performs the self-diagnosis by using the ultrasound scanner 100 by directly wearing the augmented reality glasses 40, and ultrasound self-diagnosis is performed while determining the current position of the ultrasound scanner 100 by the virtual cursor 60 shown on the display panel 46 of the augmented reality glasses 40. FIG. 1D is a diagram illustrating a fatty liver ultrasound self-diagnosis examination, FIG. 1E is a diagram illustrating a fetal ultrasound self-diagnosis examination, FIG. 1F illustrates a breast cancer self-diagnosis examination, and FIG. 1G illustrates a case of performing a carotid artery ultrasound self-diagnosis examination. Reference numerals 59a, 59b, 59c, and 59d illustrated in FIG. 1D to FIG. 1G represent examples of the ultrasound images.

FIG. 2A illustrates an example of virtual object images including a lung 51, a heart 52, a liver 53, a stomach 54, and a spleen 55 displayed with different colors for each organ as virtual interested organs 50 displayed on the display panel 46 of the augmented reality glasses. Reference numeral 60 represents that the current ultrasound scanner 100 scans the stomach 54 area by the virtual cursor.

Figure 2B:
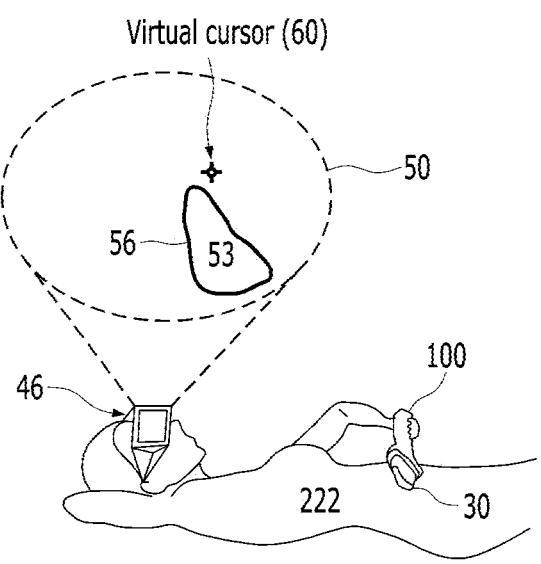

Further, FIGS. 2A and 2B illustrate examples in which the liver 53, an organ to be examined, is expressed by a border line 56. FIG. 2A illustrates an example in which peripheral interested organs other than the liver 53 are jointly displayed on the display panel 46, while FIG. 2B illustrates an example in which only the liver 53 is displayed.

Figure 2C:
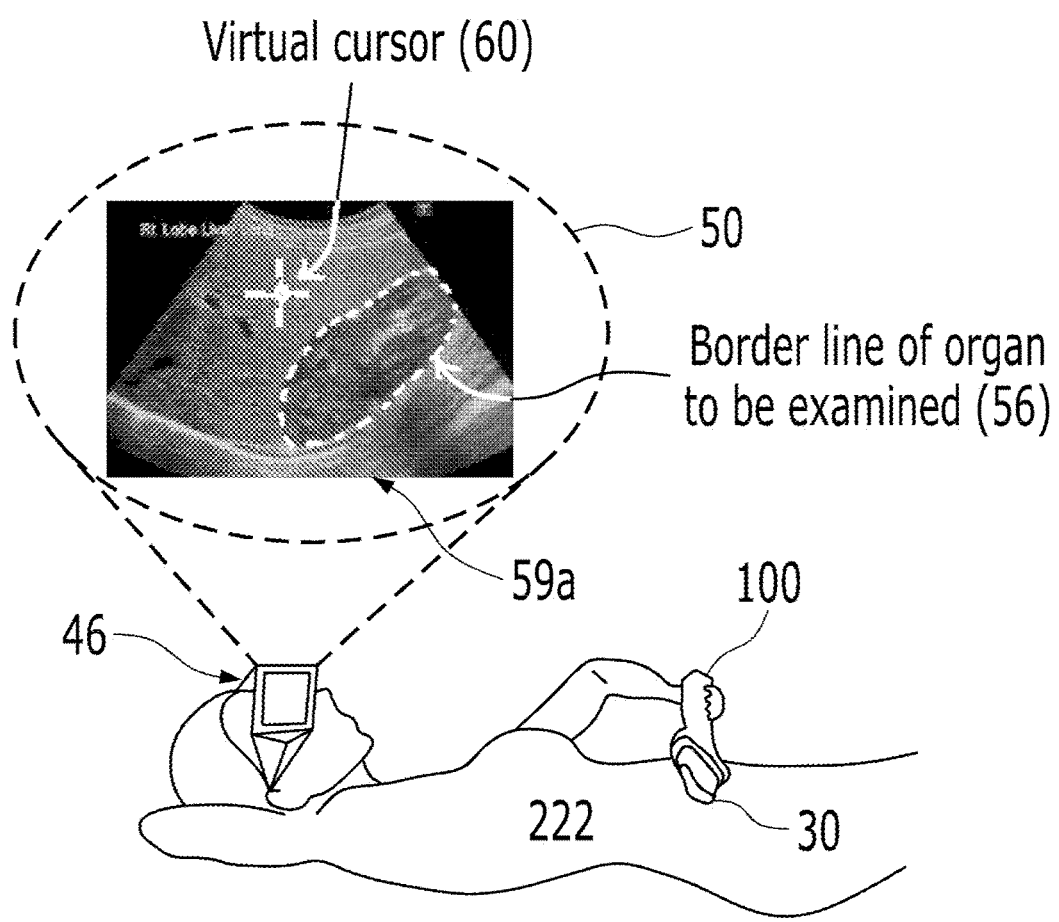

FIG. 2C illustrates a case where the organ to be examined is the liver 53, and in this case, FIG. 2C illustrates a case where the border line 56 of the organ to be examined is overlapped and displayed on the ultrasound image 59a.

FIG. 3 illustrates an example in which the liver (53) area, which is the organ to be examined blinks on/off.

On a left side, the liver (53) area is marked and displayed with a color, while on a right side, the liver (53) area is marked with a white color, so when a right image and a left image are repeatedly shown at a predetermined time interval (blink interval), an on/off blink effect is shown for the liver (53) area.

In the present disclosure, it may be desirable that in respect to the blink interval, the organ to be examined is on for 0.5 seconds and off for 0.5 seconds.

Figure 4:
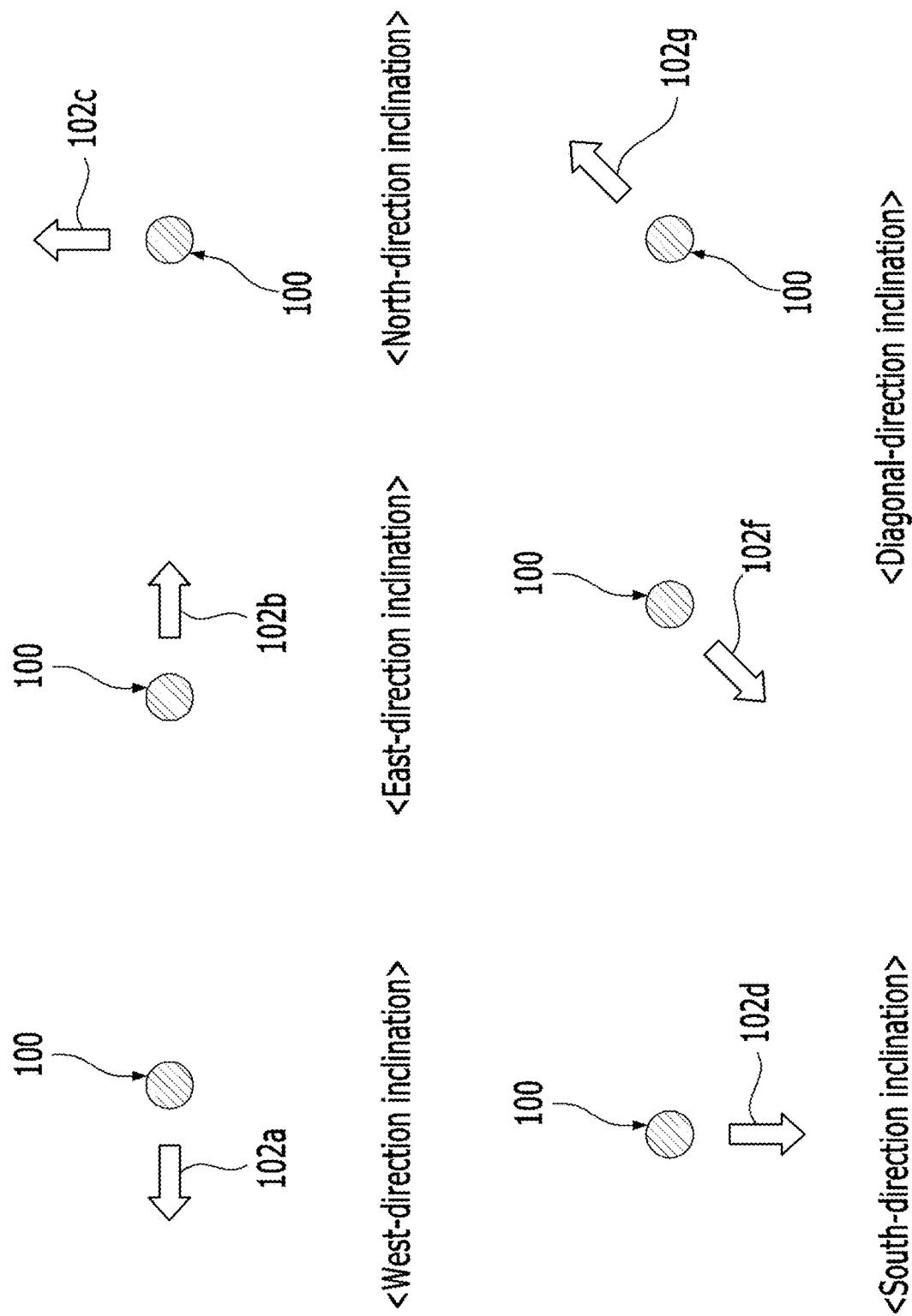
FIG. 4 is an example of an incident angle correction arrow indicating an incident angle correction direction displayed on the display panel of the augmented reality glasses according to one or more embodiments.

FIG. 4 is an example of an incident angle correction arrow indicating an incident angle correction direction displayed on the display panel 46 of the augmented reality glasses. It may be desirable that as a virtual object image for informing the person who conducts the self-diagnosis for in which direction the ultrasound scanner 100 should be inclined with respect to a current incident angle of the incident angle correction arrow, the direction of the incident angle correction arrow is displayed from a top view of the ultrasound scanner 100. For example, when the ultrasound scanner 100 should be inclined in a west direction, a west incident angle correction arrow 102a is displayed or blinks.

Reference numeral 102b represents an east incident angle correction arrow, reference numeral 102c represents a north incident angle correction arrow, reference numeral 102d represents a south incident angle correction arrow, and reference numerals 102f and 102g represent diagonal incident angle correction arrows.

Further, when the incident angle of the current ultrasound scanner matches a desired incident angle, the incident angle correction arrow disappears.

Figure 5:
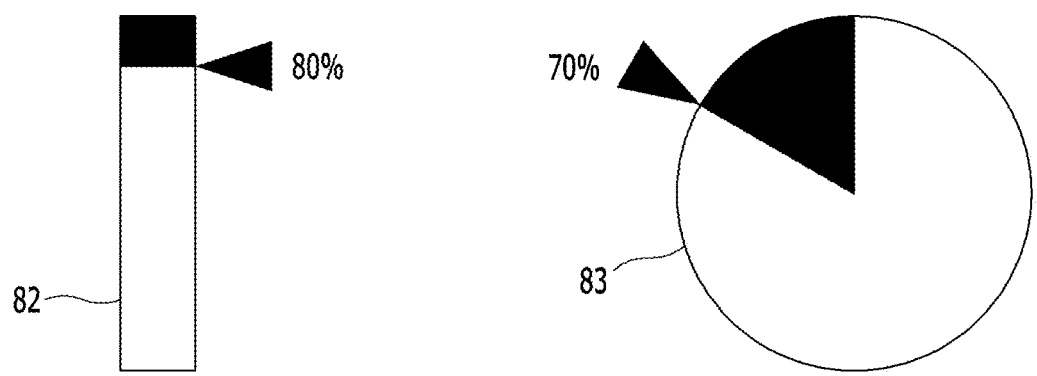
FIG. 5 is an example of representing a contact pressure of a current ultrasound scanner at a percentage ratio as compared with contact pressure information requested by a bar graph a pie graph for pressure correction information displayed on the display panel of the augmented reality glasses according to one or more embodiments.

FIG. 5 illustrates an example representing a contact pressure of the current ultrasound scanner at a percentage ratio as compared with contact pressure information requested by a bar graph 82 and a pie graph 83 for pressure correction information displayed on the display panel 46 of the augmented reality glasses.

Further, when the contact pressure of the current ultrasound scanner 100 satisfies the desired contact pressure, the bar graph 82 and the pie graph 83 disappear on the display panel 46.

Figure 6:
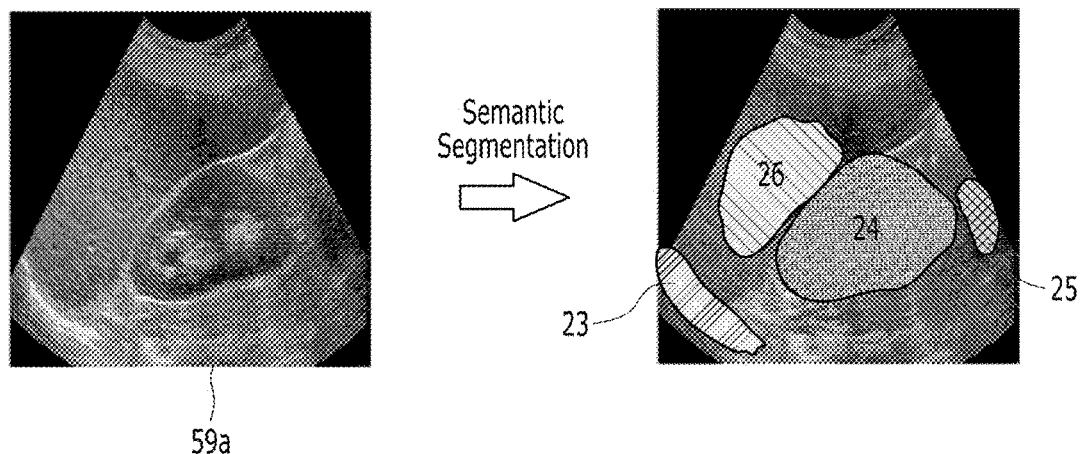
FIG. 6 is a diagram illustrating an example of a body map displaying interested organs labeled for each pixel with different colors for each organ by performing semantic segmentation for an ultrasound image of a patient obtained from the ultrasound scanner according to one or more embodiments.
Figure 7:
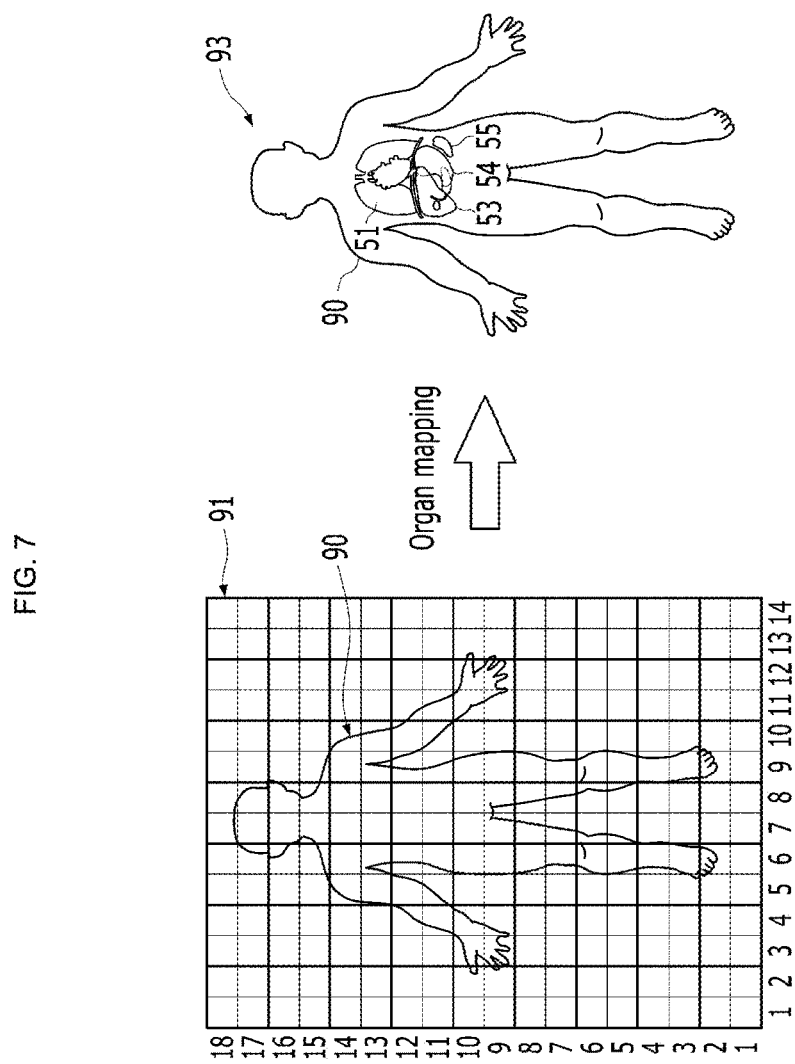
FIG. 7 illustrates an example of a body map to which virtual interested organs are mapped by considering a medical arrangement correlation of internal organs of the body on a body image obtained by a 3D camera according to one or more embodiments.

FIGS. 6 and 7 illustrate various examples of the mapper 37 of the present disclosure.

FIG. 6 illustrates an example of a body map of displaying interested organs labeled for each pixel with different colors for each organ by performing semantic segmentation for an ultrasound image 59a of a patient obtained from the ultrasound scanner 100.

Reference numeral 26 represents a liver area, reference numeral 25 represents a spleen area, reference numeral 24 represents a kidney area, and reference numeral 23 represents a diaphragm area.

FIG. 7 illustrates an example of a body map 93 to which virtual interested organs 51, 53, 54, and 55 are mapped by considering a medical arrangement correlation of internal organs of the body on a body image 90 obtained by a 3D camera 35. For smooth organ mapping, a mapping task is performed for the body image 90 by using a grid pattern 91.

To this end, first, an outline of the body is included from the body image 90, head, neck, trunk, arm, and leg parts are found, the virtual interested organs are arranged in the body image by using the head, neck, trunk, arm, and leg parts as body reference points, and a position and an area of the organ to be examined may also be known therefrom.

The body map 93 using the body reference points is advantageous when it is difficult to obtain a proper ultrasound image because the ultrasound scanner 100 has not yet been properly seated on the affected part, and the incident angle or contact pressure of the ultrasound scanner does not match properly. That is, the body map 93 using the body reference points is advantageous in securing the body map when it is difficult to perform the semantic segmentation because it is difficult to obtain a proper ultrasound image.

The body map 93 using the body reference points is advantageous in determining the position of the organ to be examined at the initial stage of use of the ultrasound scanner, that is, before stable contact of the ultrasound scanner with the affected part is made.

Figure 8:
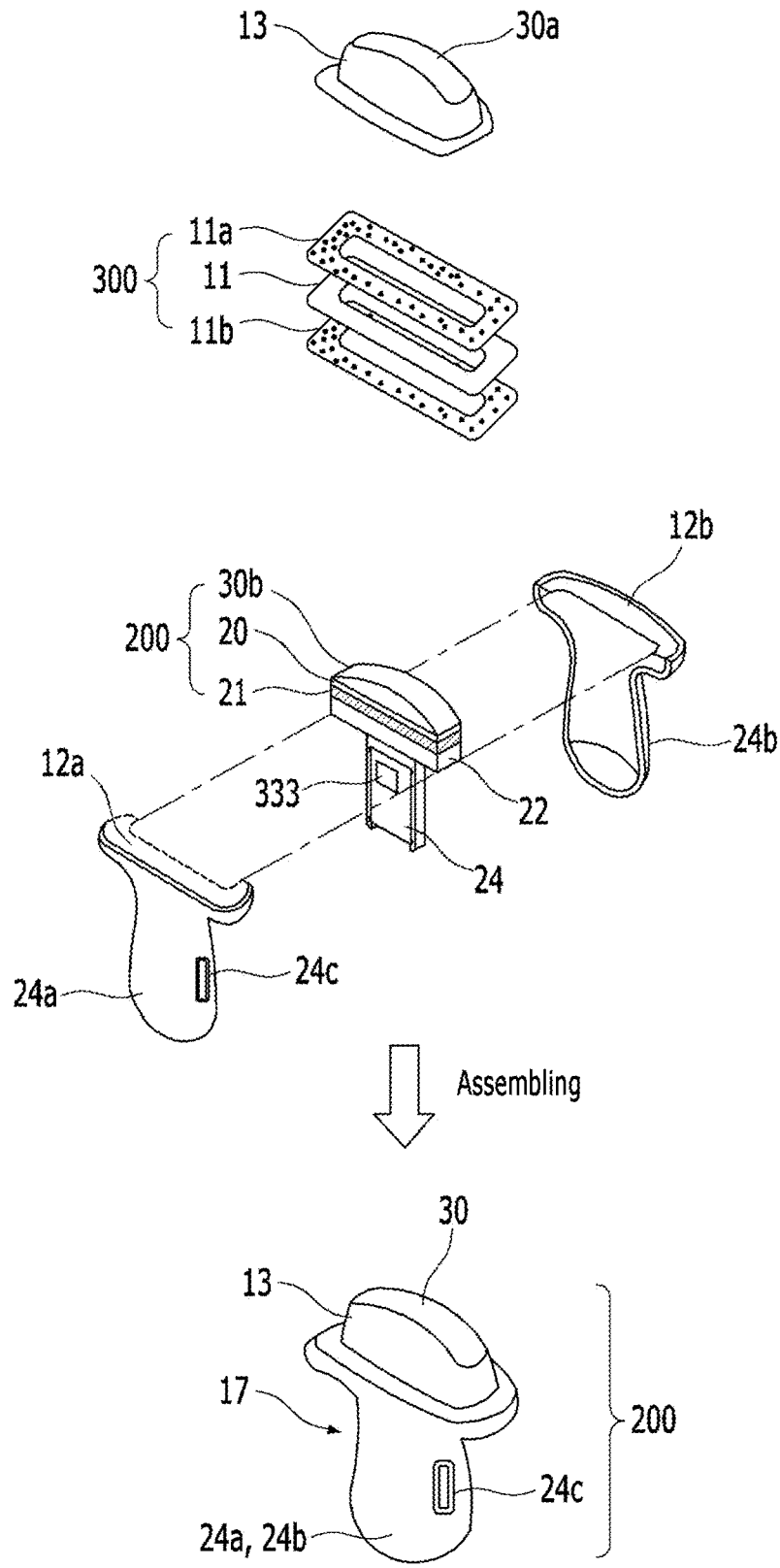
FIG. 8 is an example of installing a piezoelectric type pressure sensor measuring how strong pressure the ultrasound scanner presses an affected part inside the ultrasound scanner when an ultrasound probe contacts the affected part according to one or more embodiments.

FIG. 8 illustrates an example of installing a piezoelectric type pressure sensor 300 measuring how strong pressure the ultrasound scanner presses the affected part inside the ultrasound scanner 100 when the ultrasound probe 30 contacts the affected part.

It may be desirable that the ultrasound scanner 100 includes a main body 200 converting a signal, cases 24a and 24b and a cover 13 surrounding the main body 200, and a handle 17 provided for an examiner to grip the ultrasound scanner 100.

The handle 17 may further include an organ selection click button 24c for examination item selection of selecting an ultrasound self-diagnosis item. Whenever the organ selection click button 24c is clicked, it may be desirable that the examination item or the organ to be examined is automatically changed.

For example, in order to change the examination item, when the position of the ultrasound scanner 100 is moved to a desired organ while viewing the display panel 46 of the augmented reality glasses 40 by moving the virtual cursor 60 on the body map, and then the organ selection click button 24c is clicked, the organ to be examined is changed by the organ located on the virtual cursor 60.

The cases 24a and 24b have spaces to surround and accommodate the main body 200, and are designed so that upper surfaces may be coupled to the cover 13.

When the first case 24a and the second case 24b are assembled, the main body 200 is designed to be assembled while being included in the case, and it may be desirable that for smooth assembly of the case, a plurality of hook portions (not illustrated) corresponding to each other are arranged on side surfaces contacting the first case 24a and the second case 24b.

Further, the cover 13 is coupled to the upper surfaces of the cases 24a and 24b to cover an upper portion of the main body 200, and the upper surface of the cover 13 includes an opening 30a which allows exposure of an acoustic lens 30b during assembly. During assembly, the acoustic lens 30b is exposed through the opening 30a, so that the ultrasonic probe 30 is formed.

It may be desirable that the main body 200 includes a piezoelectric layer 21 for generating ultrasonic waves; a backing layer 22 installed to prevent the ultrasonic waves from being transmitted to the rear of the piezoelectric layer 21; a matching layer 20 installed on the upper surface of the piezoelectric layer 21; and the acoustic lens 30b installed on the upper surface of the matching layer 20.

It may be desirable that a circuit board 24 connected to electrode portions provided on both side surfaces of the piezoelectric layer 21 is installed on the rear surface of the backing layer 22.

The backing layer 22 is mounted on a lower surface of the piezoelectric layer 21, and blocks the ultrasonic waves propagating to the lower surface of the piezoelectric layer 21 by absorbing the ultrasonic waves generated by the piezoelectric layer 21 to prevent distortion of the image.

The matching layer 20 is installed on the upper surface of the piezoelectric layer 21, and reduces an acoustic impedance difference between the piezoelectric layer 21 and an object so that the ultrasonic waves generated from the piezoelectric layer 21 may be effectively transmitted to the object.

The acoustic lens 30b is installed on the upper surface of the matching layer 20, and is exposed through the opening 30a while assembled by the case to form the ultrasonic probe 30 that may be in direct contact with the affected part.

It may be desirable that the acoustic lens 30b has a convex shape in a radial direction of the ultrasonic wave in order to focus the ultrasonic waves.

Reference numeral 300 which represents a pressure sensor measuring with how strong pressure the ultrasound scanner 100 presses the affected part is constituted by a piezoelectric material 11 generating voltage which is in proportion to the pressing pressure, and cushioning materials 11a and 11b having elasticity, which are installed at upper and lower portions of the piezoelectric material. It may be desirable that the pressure sensor 300 is installed in and coupled to pressure sensor attachment portions 12a and 12b provided in the first case 24a and the second case 24b.

It may be desirable that the cushioning materials 11a and 11b are rubber or silicon. The voltage generated from the piezoelectric material 11 is measured by an electronic circuit 33 installed in the circuit board 24 to know with how strong pressure the ultrasound probe 30 presses the affected part.

The pressure sensor 300 using the piezoelectric material may be replaced with a resistance film pressure sensor and a resistance strain gauge type pressure sensor.

Figure 9A:
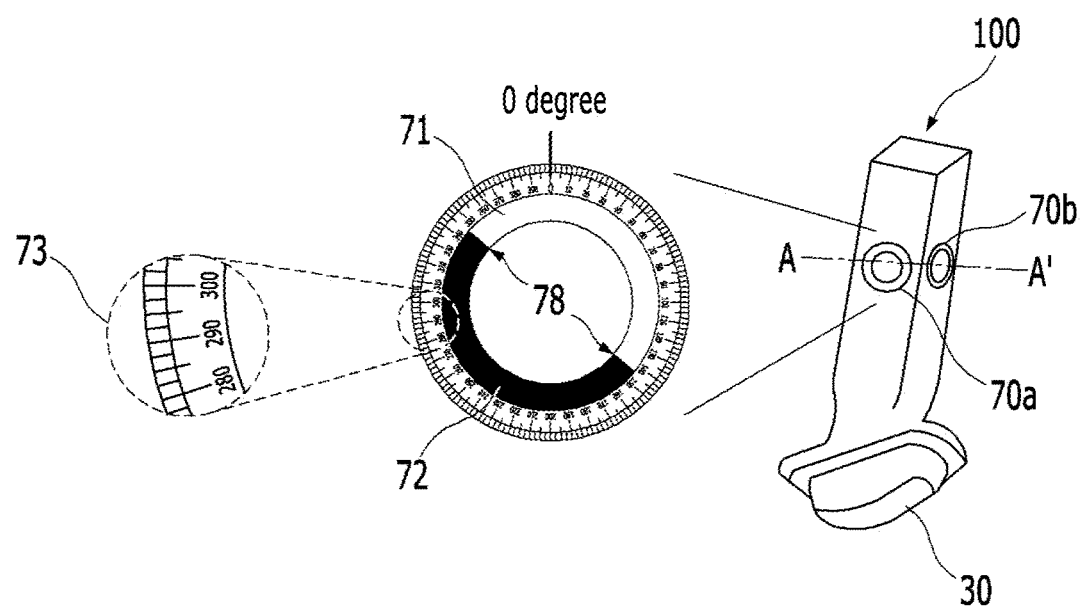
FIGS. 9A-9C is an example of an inclination sensor constituted by two liquid channels for measuring an incident angle which is an angle at which the ultrasound probe faces the surface of the affected part 3-dimensionally through an x-axis, a y-axis, and a z-axis which are present in a 3D space as a sensor sensing the incident angle of the ultrasound scanner according to one or more embodiments.
Figure 9B:
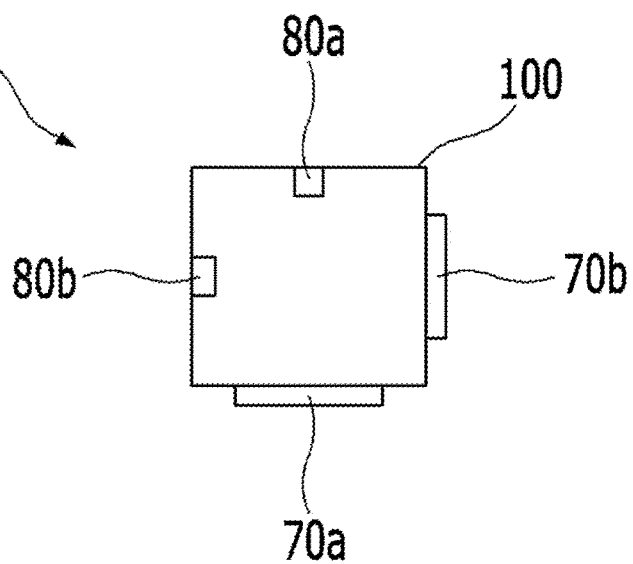
Figure 9C:
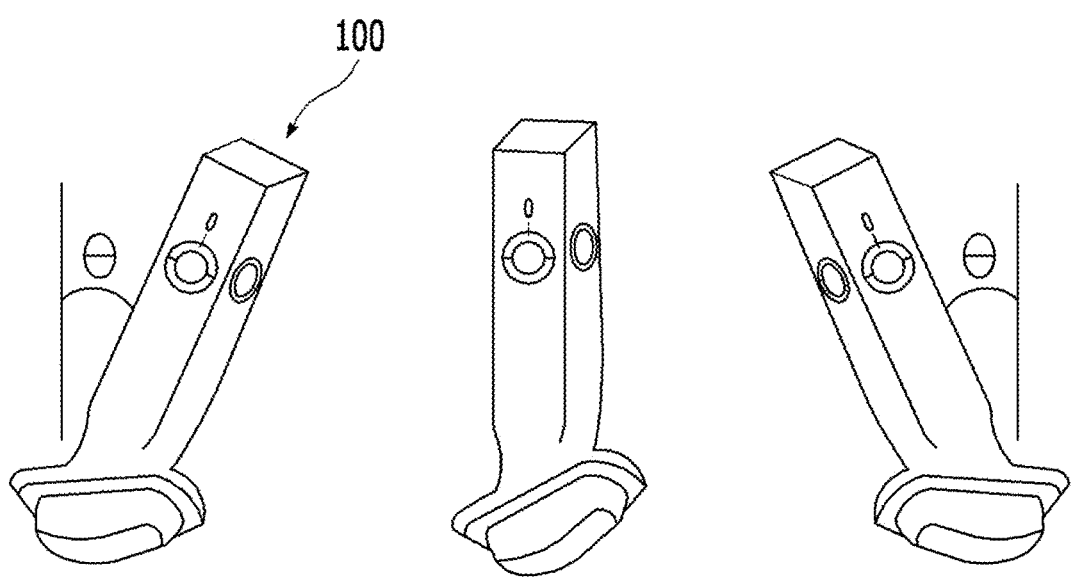

FIGS. 9A-9C illustrates an example of an inclination sensor constituted by two liquid channels 70a and 70b for measuring an incident angle which is an angle at which the ultrasound probe 30 faces the surface of the affected part 3-dimensionally through an x-axis, a y-axis, and a z-axis which are present in a 3D space as a sensor sensing the incident angle (inclination) of the ultrasound scanner 100.

According to one or more embodiments, the liquid channels 70a and 70b are provided inside the ultrasound scanner 100, and may accommodate an air layer 71 and the liquid layer 72 moving together according to the inclination of the ultrasound scanner 100, and at the same time, provide movement paths thereof.

Vision sensors 80a and 80b may determine a boundary position 78 between the air layer 71 and the liquid layer 72 in real time.

The inclination sensor is characterized in that the inclination sensor includes an angle calculator (not illustrated) that calculates the inclination of the ultrasound scanner 100 from the boundary position 78 between the air layer and the liquid layer obtained from the vision sensors 80a and 80b. It may be desirable that the angle calculator is disposed on the circuit board 24 installed inside the ultrasound scanner 100.

The incident angle of the ultrasound scanner 100 may be measured by reading the boundary position 78 between the air layer 71 and the liquid layer 72 flowing according to the inclination of the ultrasound scanner 100 with the vision cameras 80a and 80b.

FIG. 9B is a view of a cross-section A-A' of FIG. 9A, and illustrate an example in which two liquid channels 70a and 70b are designed to have a doughnut or ring shape, and the two liquid channels 70a and 70b are disposed to cross each other at 90 degrees and provided inside the ultrasound scanner 100, and the vision cameras 80a and 80b are installed on opposite sides of the two liquid channels 70a and 70b, respectively to easily observe the boundary position 78. Through this, it is possible to independently measure each of a left and right inclination and a front and back inclination of the ultrasound scanner 100.

For example, the vision camera 80a is used for observing the inclination of the liquid channel 70a immediately opposite thereto, and the vision camera 80b is used for observing the inclination of the liquid channel 70b immediately opposite thereto.

In addition, it may be desirable that a ruler 73 is provided on borders of the liquid channels 70a and 70b so that the vision cameras 80a and 80b may easily determine the inclination of the ultrasound scanner 100.

FIG. 9C illustrates examples in which the boundary position 78 between the air layer 71 and the liquid layer 72 is changed according to various inclinations of the ultrasound scanner 100.

FIG. 9C (2) illustrates a case where an incident angle q of the ultrasound scanner 100 is almost zero.

Figure 10A:
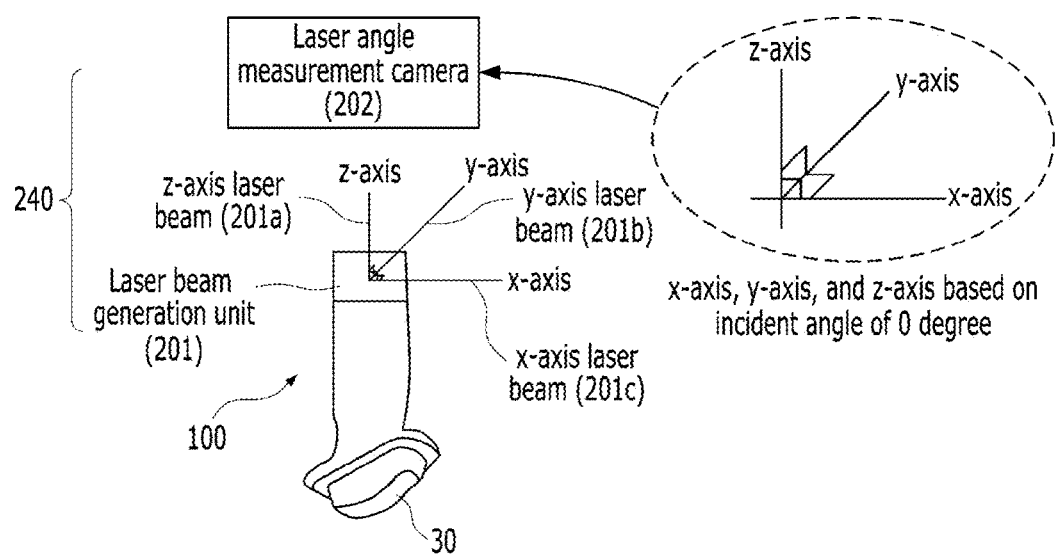
FIGS. 10A-10B illustrates an example of using a laser angle sensor constituted by a laser beam generator installed at an upper side of the ultrasound scanner, and a laser angle measurement camera observing the irradiated laser beam as one or more embodiments of the inclination sensor.
Figure 10B:
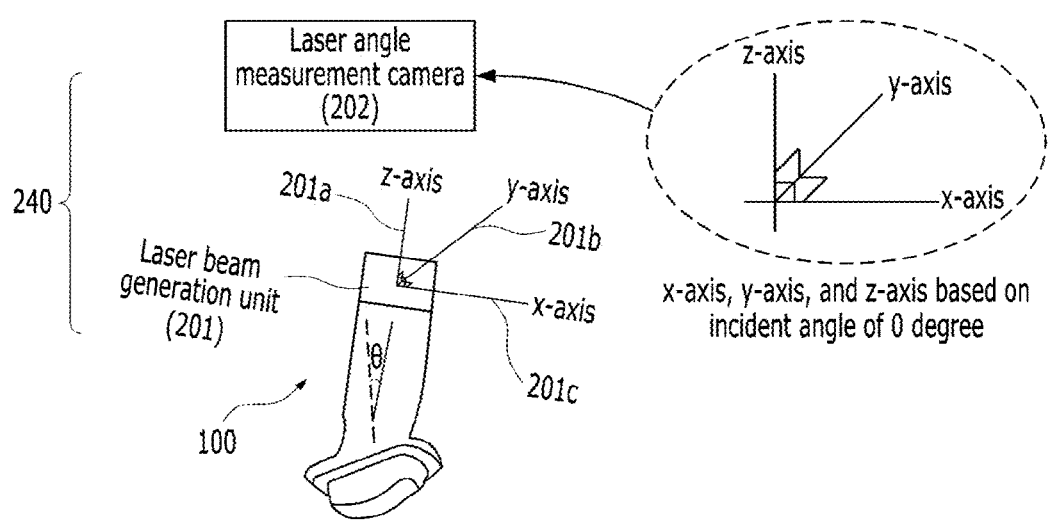

FIGS. 10A-10B is an example of the inclination sensor, in which a laser angle sensor 240 constituted by a laser beam generator 201 installed at an upper side of the ultrasound scanner 100, and a laser angle measurement camera 202 observing the irradiated laser beam.

It may be desirable that the laser beam generator 201 emits an infrared laser beam having an infrared wavelength, and the laser angle measurement camera 202 uses a camera equipped with an infrared filter so that the infrared laser beam may be observed well or uses an infrared camera of the 3D camera 35 to photograph the infrared laser beam.

It may be desirable that as the laser beam irradiated by the laser beam generator 201, laser beams are irradiated to an x-axis, a y-axis, and a z-axis which are a 3D space formed by the ultrasound scanner 100, respectively, and in this case, three laser beams 201a, 201b, and 201c are photographed by a camera capable of photographing the infrared laser beam to measure an inclined angle of the ultrasound scanner 100 with respect to 3-axis directions (x-axis, y-axis, and z-axis) in real-time.

As another aspect of the laser beam generator 201, it may be desirable that three laser beams 201a, 201b, and 201c having red, green (or purple), and blue wavelengths are used and emitted in the x-axis, y-axis, and z-axis directions which are the 3D space formed by the ultrasound scanner 100, and in this case, it may be desirable that the laser angle measurement camera 202 measures the inclined angle of the ultrasound scanner in real-time by photographing three laser beams 201a, 201b, and 201c.

FIG. 10A illustrates a case where the incident angle is 0 degrees, and FIG. 10B illustrates an example of a case where the incident angle q is 10 degrees.

FIG. 11 is an example illustrating a remote medical diagnosis method using an apparatus for correcting a posture of an ultrasound scanner for artificial intelligence-type ultrasound self-diagnosis using augmented reality glasses according to the present disclosure.

A remote medical diagnosis method using the ultrasound scanner posture correcting apparatus 600 includes assisting, by a doctor, self-diagnosis of the patient 222 while observing information on a monitor in real-time by being equipped with a communication server 203 and a communication network 402 for remotely transmitting information displayed on the display panel of the augmented reality glasses 40 to the monitor 400 of the doctor while the patient 222 performs the self-diagnosis by using the ultrasound scanner 100 by directly wearing the augmented reality glasses 40.

In this case, since the information displayed on the display panel of the augmented reality glasses 40 and the information which the doctor views on the monitor 400 are the same as each other, the doctor may easily assist the patient 222. It may be desirable that information displayed on the display panel of the augmented reality glasses 40 includes the ultrasound image and virtual object image information.

In the example illustrated FIG. 11, on behalf of the patient who is difficult to self-diagnose, the doctor 1 shares the information displayed on the display panel of the augmented reality glasses 40 through the monitor 400 in real-time to directly instruct the patient to correct the posture of the ultrasound scanner by voice through the communication network 402, thereby assisting the self-diagnosis of the patient as if the doctor is next to the patient.

Reference numeral 59b represents an example in which the ultrasound image acquired by the ultrasound scanner 100 is displayed on both the display panel of the augmented reality glasses 40 and the monitor 400 of the doctor.

According to one or more embodiments of the present disclosure, the ultrasound scanner posture correcting apparatus 600 may include the ultrasound scanner 100, the mapper 37, the scanner navigator 36, the artificial neural network 38, and the 3D camera 35. However, the configuration of the ultrasound scanner posture correcting apparatus 600 is not limited thereto.

The ultrasound scanner posture correcting apparatus 600 discriminates whether the patient has the disease and the risk degree of the disease by applying the ultrasound image of the patient acquired from the ultrasound probe 30 to the artificial neural network subjected to the deep learning training.

As an example, the ultrasound scanner 100 may include the ultrasound probe 30, the pressure sensor, the inclination sensor, and the examination item selector 31. However, the configuration of the ultrasound scanner 100 is not limited thereto.

Further, the ultrasound scanner 100 may transmit the ultrasound image which the ultrasound probe 30 acquires through the contact with the affected part of the patient. In other words, the ultrasound probe 30 of the ultrasound scanner 100 may acquire the ultrasound image from the affected part through the contact with the affected part of the patient. Further, the ultrasound scanner 100 may transmit the ultrasound image information acquired by the ultrasound probe 30 and the posture information of the ultrasound probe to the outside through the wireless transmitter.

Further, the pressure sensor may be provided inside the ultrasound scanner 100, and may measure a contact pressure between the ultrasound probe 30 and a skin surface of the affected part of the patient. For example, the pressure sensor may measure a contact pressure indicating how strong pressure presses, and scan the patient using the ultrasound probe 30.

Further, the inclination sensor may recognize an inclination angle of the ultrasound scanner 100. As an example, the inclination sensor may be used to measure the incident angle of the ultrasound scanner 100.

For example, the inclination sensor may include the liquid channels 70a and 70b, the vision sensors 80a and 80b, and the angle calculator.

Further, the liquid channels 70a and 70b may provide the movement paths of the air layer and the liquid layer moving based on an inclined degree of the ultrasound scanner 100. The liquid channels 70a and 70b may be provided inside the ultrasound scanner 100, and may accommodate the air layer 71 and the liquid layer 72 moving together according to the inclination of the ultrasound scanner 100, and at the same time, provide the movement paths thereof.

Further, the vision sensors 80*a* and 80*b* may determine the boundary position between the air layer 71 and the liquid layer 72. In real time, the vision sensors 80*a* and 80*b* may determine the boundary position 78 between the air layer 71 and the liquid layer 72.

Further, the angle calculator may calculate the inclination of the ultrasound scanner 100 from the boundary position between the air layer 71 and the liquid layer 72 acquired by the vision sensors 80*a* and 80*b*. As an example, the angle calculator may be disposed on the circuit board 24 included in the ultrasound scanner 100.

Further, the examination item selector 31 may be provided at one end of the ultrasound scanner 100. Further, the examination item selector 31 has a plurality of organ selection click buttons to designate ultrasound examination items. When user selection input information for any one of the plurality of organ selection click buttons is received by the examination item selector 31, the examination item may be automatically selected by an organ on the body map which may match the organ on the body map centered on a current position of the ultrasound scanner 100. In other words, the examination item selector 31 further includes an organ selection click button provided in the handle of the ultrasound scanner, and when a user presses the organ selection click button, the examination item may be automatically selected by the organ on the body map at a place adjacent to the current position of the ultrasound scanner.

As an example, the mapper 37 may acquire a body map in which a plurality of virtual interested organs is arranged on the body image.

Further, the mapper 37 uses the artificial neural network that acquires semantic-segmented ultrasound images labeled with different colors for each pixel with respect to the plurality of interested organs, respectively by performing the semantic segmentation based on the ultrasound image of the patient acquired by the ultrasound scanner 100.

The 3D camera 35 is provided opposite the bed 2 at which the patient 222 is located to perform the ultrasound self-diagnosis to acquire the patient's body image. Here, the mapper 37 may be implemented by a body map in which the virtual interested organs are mapped onto the body image acquired from the 3D camera 35 by considering the medical arrangement correlation of the internal organs of the body.

As an example, the scanner navigator 36 may acquire coordinates of the origin of laser beams emitted from a plurality of laser beam generators 201 provided on the upper side of the ultrasound scanner 100, and extract coordinates of the current position of the ultrasound scanner on the body image. For example, a plurality of laser acquiring apparatuses may include a laser angle measurement camera, an infrared camera, or an image sensor. In other words, the scanner navigator 36 may calculate the coordinates of the current position of the ultrasound scanner on the body map or the ultrasound image. Further, the scanner navigator 36 observes the origin coordinates of the laser beam emitted from the laser beam generator 201 with the laser angle measurement camera, the infrared camera, or the image sensor to acquire current position coordinate information of the ultrasound scanner 100 on the body image and display the current position coordinate information in the augmented reality glasses 40 by using the virtual cursor.

The augmented reality glasses 40 may include the display panel displaying the ultrasound image and the virtual object image. Here, the virtual object image may be any one or more object images selected from a virtual cursor, pressure correction information, incident angle correction information, a virtual interested organ, and an organ to be examined.

Further, the augmented reality glasses 40 may include the wireless receptor 3 42 for receiving the ultrasound image information transmitted by the wireless transmitter 1 33 and the wireless transmitter 2 39, and the posture information of the ultrasound probe 30, and the display panel 46 displaying the ultrasound images received by the wireless receptor 3 42 and the posture information of the ultrasound scanner 100.

Further, the artificial neural network 38 may perform deep-learning training by inputting ultrasound images for training. As an example, the artificial neural network 38 as a neural network that allows deep-learning training is constituted by a combination of any one or more layers or elements selected from a convolution layer, a pooling layer, a ReLu layer, a Transpose convolutional layer, an unpooling layer, a 1×1 convolutional layer, a skip connection, a global average pooling (GAP) layer, a fully connected layer, a support vector machine (SVM), a long short term memory (LSTM), Atrous convolution, Atrous Spatial Pyramid Pooling, Separable Convolution, and bilinear upsampling.

Hereinafter, a remote medical diagnosis result providing method of the present disclosure will be briefly described based on the contents described above in detail.

The remote medical diagnosis result-providing method described below may be performed by the ultrasound scanner posture correcting apparatus 600 described above. Therefore, in spite of the contents omitted below, the contents described for the ultrasound scanner posture correcting apparatus 600 may also be equally applied to the description of the remote medical diagnosis result-providing method.

First, in operation S10, the ultrasound scanner posture correcting apparatus 600 may provide whether a patient has a disease and risk degree information of the disease discriminated by using acquired ultrasound image information and the artificial neural network subjected to deep learning training to a doctor monitor.

Next, in operation S20, the ultrasound scanner posture correcting apparatus 600 may receive a remote medical diagnosis result for the patient generated by considering whether the patient has the disease and the risk degree information of the disease discriminated by using the acquired ultrasound image information and the artificial neural network subjected to deep learning training from a doctor terminal.

Next, in operation S30, the ultrasound scanner posture correcting apparatus 600 may output the remote medical diagnosis result through the augmented reality glasses 40.

In the above description, operations S10 to S30 may be further divided into additional operations or combined into fewer operations, according to an implementation example of the present disclosure. In addition, some operations may be omitted as necessary, and the order between the operations may be changed.

The present disclosure is to solve the problem in the related art, and an object of the present disclosure is to provide an apparatus for correcting a posture of an ultrasound scanner and a remote medical diagnosis method using the same, which enables even non-experts to perform easy ultrasound image diagnosis by deriving posture correction of the ultrasound scanner by transferring the posture of the ultrasound scanner to a patient through a feedback control commander to obtain the optimized postures (the incident angle, the pressure, and the location) of the ultrasound scanner for each diagnosis item and each diagnosis portion by checking postures (an incident angle, a contact pressure of an affected part, and a current location) of the ultrasound scanner.

According to an aspect of the present disclosure, there is provided an apparatus for correcting a posture of an ultrasound scanner includes an ultrasound scanner including an examination item selector designating an ultrasound examination item, an ultrasound probe acquiring an ultrasound image through contact with an affected part of a patient, and a wireless transmitter for transmitting ultrasound image information obtained by the ultrasound probe and posture information (a current position, a contact pressure, and an incident angle) of the ultrasound probe to the outside, a 3D camera observing the posture and the position of the body of the patient in three dimensions, and reproducing and configuring the resulting body image of the patient in real time, a mapper acquiring a body map in which virtual interested organs are arranged on the body image, a scanner navigator calculating the coordinates of the current position of the ultrasound scanner on the body map or the ultrasound image, a pressure sensor mechanically connected and disposed within the ultrasound scanner to measure a contact pressure indicating how strong the ultrasound probe presses and scan the affected part of the patient under pressure, an inclination sensor (tilt sensor) used to measure an incident angle of the ultrasound scanner, a speaker transferring a feedback control command to a patient by voice or inform the patient of guidance and instructions for ultrasound diagnosis by voice in order to derive the posture of the ultrasound scanner optimized for each examination item or each examination site by checking the posture information (the current position, the contact pressure, and the incident angle) of the ultrasound scanner by the scanner navigator, the pressure sensor, and the inclination sensor, an augmented reality glasses including a wireless receptor for receiving the ultrasound image information transmitted by the wireless transmitter, and the posture information of the ultrasound probe, and a display panel displaying the ultrasound images received by the wireless receptor and the posture information of the ultrasound scanner, and an artificial neural network performing deep-learning training in advance by ultrasound pictures for training, in which the artificial neural network subjected to the deep learning training is used with the ultrasound image of the patient input from the ultrasound probe to automatically discriminate whether the patient has a disease and a disease risk degree of the patient.

In the present disclosure, ultrasound examination items include diagnosis using ultrasound equipment, including fetal diagnosis, carotid artery diagnosis, breast cancer diagnosis, appendicitis diagnosis, bone density test, osteoporosis test, aortic ultrasound, prostate ultrasound examination, ultrasound examination of human organs for liver, gallbladder, bile duct, pancreas, spleen, and kidney, etc., diagnosis of thyroid tumors, and vascular Doppler ultrasonography, etc.

The 3D camera may desirably be attached to the ceiling wall above the bed on which a self-diagnostician lies.

In the present disclosure, the ultrasound probe's inclination (incident angle) is used interchangeably with the ultrasound scanner's inclination (incident angle).

In the present disclosure, the inclination of the ultrasound scanner is used interchangeably with the same meaning as the incident angle of the ultrasound scanner or the angle of the ultrasound scanner.

In the present disclosure, a patient is used interchangeably with a self-diagnosing party.

It may be desired that an organ to be examined is designated by the examination (diagnosis) item selector.

The examination item selector for selecting the ultrasound examination item uses a touch screen, these examination items are displayed in a list on the touch screen, and the examination (diagnosis) item is selected by a user's touch operation.

Another aspect of the examination item selector for selecting the ultrasound examination item is to select staring at one of the examination items listed on the display panel by an eye tracker.

The eye tracker is installed on the rim of the augmented glasses and implemented by a camera for eye tracking for observing the movement of the patient's eye, and an eye tracking algorithm for determining at which item of the examination items listed on the display panel is starred through this.

Another aspect of the examination item selector for selecting the ultrasound examination item is that the examination (diagnosis) item is automatically selected by the organ closest to the current position of the ultrasound scanner.

In the present disclosure, it may be desirable that the ultrasound pictures for training are composed of ultrasound pictures labeled by disease type and risk grade for each ultrasound examination item.

Posture information of the ultrasound scanner of the present disclosure collectively refers to information indicating the current incident angle (slope) of the ultrasound scanner with respect to the affected part, the current contact pressure of the ultrasound scanner with respect to the affected part, and the current position of the ultrasound scanner on the patient's body, the posture correction of the ultrasound scanner is the correction of the incident angle (inclination) of the ultrasound scanner desired to maintain the ultrasound scanner posture optimized according to the diagnosis item and the diagnosis site based on the posture information of the ultrasound scanner, and the pressure correction that the ultrasound scanner presses against the affected part, and position correction of ultrasound scanners.

The augmented reality glasses are characterized in that they include a display panel for showing a virtual object image to a person performing a self-diagnosis by overlapping the image of a virtual object on the ultrasound image.

The display panel of the present disclosure uses a transparent thin film transistor liquid crystal display (TFT-LCD) or a transmissive organic light emitting diode (OLED).

The virtual object image may desirably be any one or more object images selected from a virtual cursor, pressure correction information, incident angle correction information, a virtual interested organ, and an organ to be examined.

In the present disclosure, virtual interested organs may include organs to be examined, and refer to organs on a body map.

The body map of the present disclosure refers to a layout diagram in which virtual interested organs are arranged on a body image.

The virtual cursor indicates a current position of the ultrasound scanner on the body map or ultrasound image.

Another aspect of the examination item selector for selecting the ultrasound examination item is that when the user presses an organ selection click button provided on the handle of the ultrasound scanner, it may be desirable that the examination (diagnosis) item is automatically selected by the organ on the body map located at a place adjacent to the current position of the ultrasound scanner. For example, when the virtual cursor indicating the current position of the ultrasound scanner stays in the liver area on the body map, if the organ selection click button is pressed, the examination item becomes "liver examination". Further, if the examination item is intended to be changed again, the ultrasound scanner is moved to a desired organ while watching the movement of the virtual cursor position on the body map or ultrasound image, and then the organ selection click button is pressed again.

It may be desirable that the virtual interested organs or the organs to be examined are treated with translucent shading that is labeled with a different color for each organ.

The augmented reality glasses have excellent realism by superimposing an image of a virtual object on the ultrasound image and showing it as a single virtual image when an ultrasound image obtained from an ultrasound probe is displayed on a display panel to a person conducting a self-diagnosis to provide the advantage of being able to perform posture correction of the ultrasound scanner as comfortable as handling a joystick.

The virtual cursor superimposed on the ultrasound image serves as a reference for the patient when correcting the position of the ultrasound scanner, and the pressure correction information superimposed on the ultrasound image serves as a reference for the patient during the pressure correction of the ultrasound scanner, and "incident angle correction information" superimposed on the ultrasound image is a reference for the patient when correcting the incident angle of the ultrasound scanner.

Another aspect of the present disclosure is characterized in that the organ to be examined further includes a border line of the organ to be examined.

In the present disclosure, the position of the interested organ is determined by a mapper, and the determined interested organs are displayed as virtual object images using the augmented reality glasses.

It may be desirable to superimpose the virtual object image by translucent shading on the border line of the object or the object region on the ultrasound image, and in this case, the self-diagnosis person may better understand the ultrasound image to provide an advantage of being capable of conveniently correcting the position of the ultrasound scanner.

In another aspect of the present disclosure, it may be desired that the virtual cursor, the border line of the organ to be examined, or the area of the organ to be examined blinks.

In this case, the self-diagnosis person may easily determine the current position of the ultrasound scanner by the blinking virtual cursor, and it may be easily understood whether the organ to be examined corresponding to the examination item may be well found and diagnosed by determining a direction of moving the ultrasound scanner by the blinking organ to be examined.

That is, the self-diagnosis person may intuitively and easily know the degree of coordinate matching or inconsistency between the current position cursor and the organ to be examined, which is advantageous when correcting the position of the ultrasound scanner.

In the present disclosure, when the coordinates of the virtual cursor position and the organ to be examined coincide within a predetermined range, it may be desired that the blinking of the organ to be examined is stopped.

In this case, the self-diagnosis person may intuitively recognize the fact that the organ to be examined is well found, which is advantageous when correcting the position of the ultrasound scanner.

The incident angle correction information uses an incident angle correction arrow that indicates the incident angle correction direction including up, down, left, and right directions, and is a virtual object image that informs the person conducting self-diagnosis through an arrow direction indication of a method for reaching the incident angle of an ideal ultrasound scanner empirically known in advance according to the examination site and the examination item.

In the present disclosure, when the incident angle of the current ultrasound scanner does not match the desired incident angle, it may be desired that the incident angle correction arrow indicating the incident angle correction direction blinks and displayed while being overlapped with the ultrasound image on the display panel of the augmented reality glasses.

Further, when the incident angle of the current ultrasound scanner matches a desired incident angle, the incident angle correction arrow automatically disappears on the display panel.

In this case, the self-diagnosis person may intuitively and easily know whether the ultrasound scanner coincides with or does not match the desired incident angle, which is advantageous when correcting the incidence angle of the ultrasound scanner.

Another aspect of the present disclosure is characterized in that the pressure correction information provides both contact pressure information desired for the ultrasound scanner for the affected part and the current contact pressure information of the ultrasound scanner.

The contact pressure information desired in the present disclosure is ideal contact pressure information of an ultrasound scanner that is known empirically in advance according to a diagnosis site and a diagnosis item, and the desired contact pressure information may desirably be displayed by any one display method selected from a bar graph, a pie graph, or a numerical value, and it may be desirable that the current contact pressure information of the ultrasound scanner is also displayed by the same display method.

In another aspect of the touch screen, it may be desired to simultaneously display information displayed on the display panel of the augmented reality glasses on the touch screen or a mobile device including a tablet device. In this case, on behalf of the person who is difficult to self-diagnose, another person may directly perform the posture correction of the ultrasound scanner while referring to the ultrasound scanner posture information displayed on the touch screen or mobile device, so that the person performing the self-diagnosis may help with self-diagnosis.

As another option, on behalf of the self-diagnosis person, the helper may help the self-diagnosis of the self-diagnosis person by wearing the augmented reality glasses directly.

The mapper of the present disclosure is for detecting an ultrasound image including interested organs among ultrasound images obtained from the ultrasound scanner, and it may be desired to use an artificial neural network which is trained in advance by the ultrasound images labeled with semantic segmentation for the interested organs, and then is used for acquiring the semantic-segmented ultrasound image labeled for each pixel with different colors for each interested organ by performing the semantic segmentation for the ultrasound image of the patient given from the ultrasound scanner, and the organ to be examined may be included in interested organs discovered while ultrasound-scanning the affected part of the patient, and in this case, the self-diagnosis person may determine the position and the area of the organ to be examined on the ultrasound image by color marking.

The semantic segmentation is an artificial intelligence neural network that classifies the position of a specific object in a given image in units of pixels and divides the object from other objects.

In the present disclosure, the interested organ or the organ to be examined may desirably be any one or more organs selected from the heart, liver, aorta, kidney, spleen, diaphragm, bone, breast, uterus, fetus, placenta, carotid artery, thyroid gland, blood vessels and tissues permitted to be subjected to ultrasound examination by a Doppler effect, prostate, and human body organs.

The artificial intelligence neural network of the present disclosure uses a Convolutional Neural Network (CNN) and a Recurrent Neural Network (RNN).

In the present disclosure, the artificial neural network as a neural network which allows deep-learning training is constituted by a combination of any one or more layers or elements selected from a convolution layer, a pooling layer, a ReLu layer, a Transpose convolutional layer, an unpooling layer, a 1×1 convolutional layer, a skip connection, a global average pooling (GAP) layer, a fully connected layer, a support vector machine (SVM), a long short term memory (LSTM), Atrous convolution, Atrous Spatial Pyramid Pooling, Separable Convolution, and bilinear upsampling. It may be desirable that the artificial intelligence neural network further includes a calculator for batch normalization calculation in front of the ReLu layer.

The semantic segmentation of the present disclosure is an artificial intelligence neural network that classifies the interested organs in units of pixels where they are included and divides them from other objects when there is an interested organ in a given ultrasound image, and pre-trained by color-labeled standard organ ultrasound image database labeled with different colors for respective interested organs.

The standard organ ultrasound image database may desirably be composed of ultrasound pictures of a normal person without a disease in the vicinity of the organ of interest.

Another aspect of the mapper of the present disclosure is implemented by a body map in which virtual interested organs are mapped onto the body image acquired by the 3D (three dimension) camera by considering a medical arrangement correlation of internal organs of a human body.

The body map may desirably be an image labeled using different colors for major organs of interest, such as heart, breast, carotid artery, kidney, and liver, on the body image, and the virtual interested organs are labeled on the body image acquired from the 3D camera by a physical arrangement situation of the internal organs of the human body.

To this end, first, an outline of the body is included from the body image, head, neck, trunk, arm, and leg parts are found, the virtual interested organs are arranged in the body image by using the head, neck, trunk, arm, and leg parts as body reference points.

When registering a patient through a website on the Internet that works in conjunction with an ultrasound scanner, the positions of the virtual interested organs are determined by calculating the medical arrangement correlation of the internal organs of the human body based on patient information including input patient's sex, age, height, weight, and waist size, and body reference points.

The patient authentication may desirably be performed by any one method selected from face recognition, fingerprint recognition, voice recognition, ID authentication, and authentication method through a mobile device registered at the time of patient registration.

In another aspect of the mapper of the present disclosure, when obtaining an ultrasound image is difficult and it is thus difficult to perform semantic segmentation, a body map is acquired in which virtual interested organs are mapped onto a body image obtained by a three dimension (3D) camera by considering a medical arrangement correlation of internal organs of a human body, and a body map labeled for each pixel with different colors for each organ is obtained by performing semantic segmentation for an ultrasound image of a patient given from an ultrasound scanner when it is possible to acquire the ultrasound image.

The 3D camera provides depth information in addition to two-dimensional image information for the patient's body, the mapper obtains a body map according to the patient's body posture and body position, and the wireless transmitter wirelessly transmits the body map to the augmented reality glasses.

In this case, it may be desired that the augmented reality glasses not only display the body map on the display panel, but also display the organs to be scanned by the ultrasound scanner by blinking and displaying them to the patient based on the body map and diagnosis items to induce the position to be determined, and to display the desired ultrasound scanner contact pressure information and incident angle correction arrow as a virtual object image on the display panel.

In the augmented reality glasses of the present disclosure, it may be desirable to display the desired contact pressure and desired incident angle correction information together with the posture information (current position, current contact pressure, current incident angle) of the ultrasound scanner on the display panel of the augmented reality glasses, and in this case, the self-diagnosis person may easily recognize at which location, at which incident angle, and with how much contact pressure to use the ultrasound scanner, thereby enabling self-diagnosis.

The 3D camera in the present disclosure may desirably be constituted by an infrared (IR) laser projector for projecting and radiating Structured Light (SL) light composed of tens of thousands of specific patterns (straight lines, dot patterns or grid patterns) onto the patients body, an infrared camera for measuring the depth by analyzing the degree of deformation of the pattern according to the shape of the patient's body surface for the emitted laser pattern, and a 3D computing device for calculating the measured depth, and then synthesizing the patient's two-dimensional body image taken by the image sensor, and deriving a three-dimensional body image.

The pressure sensor of the present disclosure refers to a sensor that measures how much pressure the ultrasound scanner presses against the affected part when the ultrasound probe is in contact with the affected part, and is desired to secure a good ultrasound image for maintaining a contact pressure determined by clinical experience according to the diagnosis item and diagnosis location, and use any one pressure sensor selected from a resistance film pressure sensor a piezoelectric type pressure sensor, and a resistance strain gauge type pressure sensor.

As the desired contact pressure, it may be desirable to use a contact pressure value determined by the above clinical experience.

In the resistance film pressure sensor, it may be desirable that a glass plate and a special film laid in parallel at a predetermined interval are coated with a resistance film to face each other, and it may be desirable to measure the pressure by using a principle in which the facing resistance films contact each other by pressing the special film. It may be desirable to use a carbon nanotube (CNT) as the resistance film.

As the resistance film pressure sensor, a force sensitive resistor (FSR) pressure sensor may be desired.

In the FSR pressure sensor, a structure may be desired in which a space layer that creates a spatial gap is placed in the center, and a Flexible Printed Circuit (FPC) Layer with a printed circuit is placed on the upper portion of the space layer, while on the lower side, a conductive film layer coated with a conductive material is placed, and when a force is applied from above, more parts of the FPC comes into contact with the conductive film, and the resistance value of the sensor decreases, so that pressure may be measured. As the FSR sensor, it may be desirable that a circuit on the FPC layer is printed in a matrix structure so as to measure the two-dimensional pressure distribution.

The piezoelectric type pressure sensor uses a piezoelectric effect that generates electricity when pressure is applied from the outside, and may desirably be constituted by a piezoelectric material and electrodes attached to both ends of the piezoelectric material to obtain an electrical output corresponding to the input pressure.

As the resistance strain gauge type pressure sensor, a grid-type resistance structure in which resistance change is induced by a difference in geometric length or thickness when a strain occurs under tension or pressure may be desired, and the grid-type resistance structure is more used in connection with a Wheatstone bridge circuit. The Wheatstone bridge circuit may be desired because it is possible to measure the pressure change with good sensitivity even if the resistance change is small.

The inclination sensor of the present disclosure is a sensor for detecting the inclination (incident angle) of the ultrasound scanner, and through the x-axis, y-axis, and z-axis existing in three-dimensional space, the incident angle which is the angle facing the surface of the affected part of the ultrasound probe is measured in 3D. The self-diagnosis person adjusts the incident angle of the ultrasound scanner to improve the quality of the ultrasound image obtained from the affected part.

It may be desired that the inclination sensor of the present disclosure adopts any one selected from a gyro sensor, an accelerometer, and a geomagnetic sensor as an inclinometer for measuring the inclination angle of the ultrasound scanner in a three-dimensional space or combines and adopts the sensors.

The gyro sensor is a sensor that measures angular velocity, which is the physical displacement of yaw (z-axis rotation), roll (x-axis direction rotation, left-right rotation), and pitch (y-axis direction rotation, vertical rotation), and the accelerometer is used for measuring the respective accelerations in the x-axis, y-axis and z-axis directions, and the gyro sensor and the accelerometer adopt micro electro mechanical systems (MEMS) manufactured by integrating micro mechanical components and an electronic circuit for converting the physical displacements of these mechanical components into electrical signals on a common silicon substrate.

The geomagnetic sensor may desirably be made using a Hall effect, a Magneto-Resistive Effect (MR) effect, or a Magneto Impedance (MI) effect.

As another aspect of the inclination sensor of the present disclosure, a laser angle sensor is used, which is constituted by a plurality of laser beam generators installed at an upper side of the ultrasound scanner, and a laser angle measurement camera visually observing the plurality of emitted laser beams.

It may be desirable that the plurality of laser beam generators emits an infrared laser beam having an infrared wavelength, and the laser angle measurement camera uses a camera equipped with an infrared filter so that the infrared laser beam may be observed well or uses an infrared camera of the 3D camera to photograph the infrared laser beam.

It may be desirable that as the laser beams irradiated by the plurality of laser beam generators, laser beams are formed by three laser beams irradiated perpendicular to each other in an x-axis, a y-axis, and a z-axis which are a 3D space formed by the ultrasound scanner, respectively, and in this case, three laser beams are photographed by a camera capable of photographing the infrared laser beam to measure an inclined angle of the ultrasound scanner with respect to 3-axis directions (x-axis, y-axis, and z-axis) in real time.

As another aspect of the plurality of laser beam generators, it may be desirable that three laser beams having red, green (or purple), and blue wavelengths are used and emitted in the x-axis, y-axis, and z-axis directions which are the 3D space formed by the ultrasound scanner, and in this case, it may be desirable that the laser angle measurement camera measures the inclined angle of the ultrasound scanner in real time by photographing three laser beams.

When the ultrasound scanner is inclined, the laser beams in the three-axis directions (x-axis, y-axis, and z-axis) are also inclined jointly, and as a result, it is possible to measure the incident angle (inclination) of the ultrasound scanner in the 3D space through measurement of the inclined degrees of three laser beams.

In another aspect of the scanner navigator of the present disclosure, by observing and determining the coordinates of the origin of the laser beam emitted from the laser beam generator with a laser angle measuring camera, an infrared camera or image sensor, the current position coordinates of the ultrasound scanner on the body image are obtained and wirelessly transmitted to the augmented reality glasses.

It may be desirable to display the current position coordinate information of the ultrasound scanner by using a virtual cursor on the display panel of the augmented reality glasses to be superimposed on the body map or display the current position coordinate information being superimposed on the ultrasound image.

Another aspect of the inclination sensor of the present disclosure includes liquid channels provided in the ultrasound scanner, including an air layer and a liquid layer moving together according to the inclination of the ultrasound scanner, and at the same time, providing movement paths of the air layer and the liquid layer, vision sensors for determining a boundary position between the air layer and the liquid layer in real time, and an angle calculator calculating the inclination of the ultrasound scanner from the boundary position between the air layer and the liquid layer obtained from the vision sensors.

Further, the inclination sensor reads a boundary between the air layer and the liquid layer flowing according to the inclination of the ultrasound scanner with the vision camera to measure the incident angle of the ultrasound scanner.

The liquid channel has a doughnut or ring shape, and two liquid channels are provided inside the ultrasound scanner, and the two liquid channels are disposed inside the ultrasound scanner to cross each other at 90 degrees. The two liquid channels measure the left and right inclination and the front and back inclination of the ultrasound scanner, respectively.

The liquid may desirably be an oil component in which evaporation does not occur, and it may be desired to fill the liquid channel with an air layer of 50% and an oil of 50%.

In addition, it may be desirable that a pigment is added to the liquid component so that the boundary between the air layer and the liquid layer may be easily recognized by a vision camera.

The wireless transmission/reception connection of the present disclosure may desirably be made by a Wi-Fi Internet connection.

Another aspect of the present disclosure provides a remote medical diagnosis method using an ultrasound scanner posture correcting apparatus according to the present disclosure, in which the ultrasound scanner posture correcting apparatus further includes an artificial intelligence-type virtual doctor which automatically analyzes an ultrasound image obtained from a patient and performs remote diagnosis with a doctor, and which includes: correcting a position of the ultrasound scanner, correcting an incident angle of the ultrasound scanner, correcting a pressure of the ultrasound scanner, providing an automatic analysis result for whether an organ to be examined has a disease to a mobile terminal of the patient and a mobile terminal of a doctor in charge through an Internet network, and providing a consultation service with the doctor in charge as desired.

According to one or more embodiments, a remote medical diagnosis method using an ultrasound scanner posture correcting apparatus may include, the ultrasound scanner posture correcting apparatus may further include a communication server and a communication network for remotely transmitting information displayed on a display panel of augmented reality glasses to a monitor of a doctor, result providing method performed by an apparatus for correcting a posture of an ultrasound scanner may include: remotely transmitting the information displayed on the display panel of the augmented reality glasses to the monitor of the doctor while the patient performs the self-diagnosis by using the ultrasound scanner, and sharing the information displayed on the display panel of the augmented reality glasses on the monitor in real time, and observing, by the doctor, the information displayed on the monitor in real time, and assisting, by the doctor, the self-diagnosis of the patient while instructing the patient to correct the posture of the ultrasound scanner by voice through the communication network.

According to the solver of the present disclosure, provided an apparatus for correcting a posture of an ultrasound scanner, and a remote medical diagnosis method using the same, which are used for self-diagnosis by using an ultrasound device in person without the aid of a doctor by the aid of artificial intelligence in an ultrasound image processing field, for acquiring a good-quality ultrasound image which is easy for ultrasound diagnosis by deriving posture correction of the ultrasound scanner by transferring a feedback control command to a patient through a speaker and augmented reality glasses in order to provide a posture of an optimized ultrasound scanner, a contact pressure of the ultrasound scanner with an affected area, and a position of the ultrasound scanner to a patient who performs self-diagnosis by checking the posture of the ultrasound scanner, the contact pressure of the ultrasound scanner with the affected area, and a current location of the ultrasound scanner.

The ultrasound scanner posture correcting apparatus, examination item selector, ultrasound probe, wireless transmitter, wireless receptor, 3D camera, scanner navigator, mapper, artificial neural network, ultrasound scanner, augmented reality glasses in FIGS. 1-11 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An ultrasound scanner apparatus using augmented reality glasses, the ultrasound scanner apparatus comprising:
    an ultrasound scanner, the ultrasound scanner comprising:
        an ultrasound probe configured to acquire an ultrasound image of a patient;
        a camera for capturing a body image of the patient;
        a mapper configured to acquire a body map in which virtual organs are arranged on the body image;
        a scanner navigator configured to calculate a current position coordinate of the ultrasound probe on the body map;
    augmented reality glasses configured to display the ultrasound image and the virtual organs; and
    an artificial neural network configured to determine whether the patient has a disease and a risk degree of the disease,
    wherein the ultrasound scanner further comprises:
        an examination item selector configured to designate an ultrasound examination item;
        a pressure sensor configured to measure contact pressure between the ultrasound probe and the patient's skin surface;
        a tilt sensor configured to recognize a tilt angle of the ultrasound scanner; and
        a wireless transmitter for transmitting the tilt angle and the contact pressure for display of a tilt angle correction and contact pressure correction by the augmented reality glasses; and
    wherein the tilt sensor comprises:
        liquid channels configured to provide movement paths for an air layer and a liquid layer based on an inclined degree of the ultrasound scanner; and
        vision sensors to observe a boundary position between the air layer and the liquid layer; and
    wherein the examination item selector further comprises an organ selection click button configured to:
        automatically select one of the virtual organs adjacent to the current position coordinate of the ultrasound probe.

2. The ultrasound scanner apparatus of claim 1, wherein the augmented reality glasses are configured to display a virtual sensor on the current position coordinate.

3. The ultrasound scanner apparatus of claim 1, wherein the augmented reality glasses are configured to display one or more of the virtual organs, pressure correction information, and incident angle correction information.

4. The ultrasound scanner apparatus of claim 1, wherein the mapper is further configured to:
    acquire semantic-segmented ultrasound images of internal organs.

5. The ultrasound scanner apparatus of claim 1, wherein the virtual organs are mapped onto the body image based on a medical arrangement correlation of internal organs.

* * * * *